(12) United States Patent
Liu

(10) Patent No.: US 11,454,805 B2
(45) Date of Patent: Sep. 27, 2022

(54) SURGICAL LENS CLEANING DEVICE

(71) Applicant: Medabotics, Inc., Knoxville, TN (US)

(72) Inventor: Xiaolong Liu, College Park, MD (US)

(*) Notice: Subject to any disclaimer, the term of this patent is extended or adjusted under 35 U.S.C. 154(b) by 472 days.

(21) Appl. No.: 16/530,028

(22) Filed: Aug. 2, 2019

(65) Prior Publication Data

US 2021/0033854 A1 Feb. 4, 2021

(51) Int. Cl.
*A47L 1/00* (2006.01)
*G02B 27/00* (2006.01)
*A61B 90/70* (2016.01)
*B08B 1/00* (2006.01)

(52) U.S. Cl.
CPC .......... *G02B 27/0006* (2013.01); *A61B 90/70* (2016.02); *B08B 1/006* (2013.01); *B08B 1/008* (2013.01); *A61B 2090/701* (2016.02)

(58) Field of Classification Search
CPC ... G02B 27/0006; A61B 90/70; B08B 27/006; B08B 1/008
USPC .......... 15/250, 361, 250.361, 250.34, 250.36
See application file for complete search history.

(56) References Cited

U.S. PATENT DOCUMENTS

| | | | | |
|---|---|---|---|---|
| 9,763,567 | B2* | 9/2017 | O'Prey | A61B 1/126 |
| 2009/0105543 | A1 | 4/2009 | Miller et al. | |
| 2009/0240111 | A1* | 9/2009 | Kessler | A61B 1/00032 |
| | | | | 600/155 |
| 2009/0264703 | A1 | 10/2009 | Pribanic | |
| 2013/0209079 | A1* | 8/2013 | Alexander | B60R 11/04 |
| | | | | 396/25 |
| 2014/0094650 | A1* | 4/2014 | Schaning | A61B 17/29 |
| | | | | 600/104 |
| 2016/0315564 | A1* | 10/2016 | Kotani | B60S 1/566 |

OTHER PUBLICATIONS

Hironori Tatsuki, Takehiko Yokobori, Chika Katayama, Ryuji Kato, Ryo Takahashi, Katsuya Osone, Takahiro Takada, Reina Yajima, Yoko Motegi, Hiroomi Ogawa, Takaaki Fujii, Kenshirabe, Hiroyuki Kuwano, and Takayuki Asao, A novel one-step lens cleaning device using air and water flow for endoscopic surgery, PLOS ONE, 13:1-9, Jul. 2018.

J.T. Calhoun and J.A. Redan, Elimination of laparoscopic lens lens fogging using directional flow of CO2, JSLS: Journal of the Society of Laparoendoscopic Surgeons, 18(1):55, 2014.

Davey Kreeft, Ewout Aart Arkenbout, Paulus Wilhelmus Johannes Henselmans, Wouter R. Van Furth, and Paul Breedveld, Review of techniques to achieve optical surface cleanliness and their potential application to surgical endoscopes. Surgical Innovation, 24(5):509-527, 2017.

* cited by examiner

*Primary Examiner* — Joseph J Hail
*Assistant Examiner* — Shantese L McDonald
(74) *Attorney, Agent, or Firm* — Robinson IP Law, PLLC

(57) ABSTRACT

A lens cleaning device includes: a housing shaped to fit over an end of a camera lens; a wiper movably attached to the housing, the wiper movable across the housing from a first position adjacent a first side of the housing to a second position adjacent a second side of the housing; and at least one SMA wire mechanically associated with the wiper. When the SMA wire is activated, the wiper is moved between the first position and the second position of the housing such that the wiper sweeps debris from a field of view of the camera lens.

20 Claims, 18 Drawing Sheets

Smoke Block   Fluid Contamination

SURGICAL LENS CLEANING DEVICE

FIELD

This disclosure relates to the field of surgical devices. More particularly, this disclosure relates to a device for cleaning a lens of a surgical instrument used for minimally invasive surgery.

BACKGROUND

Clear visualization of the surgical field in minimally invasive surgery (MIS) is vitally important for the surgeon's operation efficiency and the patient's safety. Surgical scope cameras have been developed with various dimensions, flexibility, and controllability to reach inside human bodies for various MIS procedures, such as laparoscopic, endoscopic, bronchoscopic, arthroscopic, and thoracoscopic. Surgeons manipulate surgical instruments to carry out surgical procedures solely based on the visual guidance of these scope cameras. Uninterrupted and clear visual guidance is critical to the success of all these surgeries.

However, clarity of a visual field of a surgical scope camera 1 can easily be impaired by contaminated lenses due to vapor condensation, particle debris, rinsing fluid, and body fluid 2; or accumulated smoke 3 caused by electrocautery during surgery as shown in FIG. 1. According to clinical studies, more than 37% of laparoscopic surgery time is done with impaired rigid laparoscopes due to contamination of camera lenses that is considered troublesome by 68% surgeons. About 3% extra time during laparoscopic surgery is required to externally clean the blinded camera lenses, which increases the procedure length and surgery cost. More seriously, the distraction may affect a surgeon's judgment, and cause patient injury. A visually impaired rigid laparoscope could be removed and cleaned externally. However, the situation for flexible scope cameras which reach deep inside body cavity or for remotely controlled robotic surgical devices could be catastrophic for both patients and surgeons.

For example, one most recent robotic surgery accident, which took place in Freeman Hospital, Newcastle, UK and was reported on Nov. 6, 2018, caused a patient death partially due to a blinded robotic camera. The incorrectly sutured mitral valve leaked blood that blinded the robotic camera. The surgeon was compelled to shift to open-chest surgery and missed the best timing for correction which resulted in death of the patient. With the tremendous success of rigid laparoscopes in MIS, growing attention has been drawn to improve impaired vision during surgery.

The most common solution for cleaning rigid laparoscopes is to remove them from the body cavity and to wipe contaminated lenses externally. This remove-and-clean procedure significantly interrupts surgical flow, reduces a surgeon's operation efficiency and potentially jeopardizes patient safety. Chemical coatings with hydrophobicity and/or lipophobicity can alleviate camera lenses to be contaminated by fogging and/or viscous body fluid, but successful contamination prevention cannot be guaranteed. To enable reliable lens contamination removal without taking laparoscopes out of the body cavity, passive and active in vivo lens cleaning techniques have been introduced. Passive methods include redirecting a contaminated laparoscope to interact with in vivo wiping stations, such as extendable swab devices or wiping sleeves. These devices can be deployed in the body cavity through another incision independently or by being attached on other surgical instruments. For the purpose of reducing the number of body incisions, laparoscopic cannula designs with swabs/wipers at the distal ends were developed for lens cleaning by initiating a laparoscope's axial reciprocating stroke. These active methods enable laparoscopes to remain in situ by running fluid or gas flows through a laparoscope's overtube for lens cleaning, smoke evacuation or even debris prevention. The pressor rinsing fluid and gas are generated by an external pumping machine in connection with a laparoscope's overtube. Research efforts so far have addressed separate passive and active solutions that are dedicated to rigid laparoscopes for visual clarity. However, the state-of-the-art solutions are inapplicable to the advanced fully insertable and flexible surgical robotic cameras in which a unified multi-functional active clear vision mechanism is imperative.

What is needed, therefore, is a modular surgical lens cleaning device that functions to remove lens soiling and prevent debris from gathering on the lens to maintain visual clarity of robotic surgical cameras inside a body cavity.

SUMMARY

The above and other needs are met by a lens cleaning device that removes lens soiling and prevent debris from gathering on the lens to maintain visual clarity of robotic surgical cameras inside a body cavity. In a first aspect, a lens cleaning device comprising: a housing shaped to fit over an end of a camera lens; a wiper movably attached to the housing, the wiper movable across the housing from a first position adjacent a first side of the housing to a second position adjacent a second side of the housing; and at least one SMA wire mechanically associated with the wiper. When the SMA wire is activated, the wiper is moved between the first position and the second position of the housing such that the wiper sweeps debris from a field of view of the camera lens.

In one embodiment, the wiper is secured to the housing at a hinge. In another embodiment, the lens cleaning device further includes a bias spring coupled at a first end to the housing and at a second end to the wiper, the bias spring biasing the wiper towards one of the first position and the second position on the housing.

In yet another embodiment, the wiper includes a wiper layer located towards a center of the wiper and along a length of the wiper, the wiper layer extending below the wiper and into contact with a lens surface; the at least one SMA wire associated with the wiper comprising a first set of one or more SMA wires located on a first side of the wiper layer and a second set of one or more SMA wires located on a second side of the wiper. Activation of the first set of one or more SMA wires urges the wiper towards the first position and wherein activation of the second set of one or more SMA wires urges the wiper towards the second position.

In one embodiment, the lens cleaning device further includes a first reinforcement layer on the first side of the wiper layer and a second reinforcement layer on the second side of the wiper layer.

In another embodiment, the lens cleaning device further includes a slide track located around a portion of the housing; a slide bar located on an end of the wiper and slidably engaged with the slide track. The slide bar slides along a length of the slide track when the wiper moves between the first position and the second position. In yet another embodiment, the lens cleaning device further includes a first magnet proximate a first end of the slide track; and a second magnet proximate a second end of the slide track. The slide bar is formed of a ferrous material; and the first magnet releasably anchors the wiper in the first position. The second magnet releasably anchors the wiper in the second position.

In one embodiment, when the wiper is in the first position and the second position, the wiper is substantially within a side edge of the housing such that the wiper does not substantially obstruct a field of view of the camera. In another embodiment, the housing further includes one or more gaps formed in sides of the housing such that debris swept by the wiper is evacuated from the housing. In yet another embodiment, the housing further includes a cover lens located on the housing, wherein the wiper contacts the cover lens when the wiper moves between the first position and the second position. In one embodiment, the cover lens further includes a hydrophobic layer formed on an upper surface thereof.

In a second aspect, a lens cleaning device includes: a housing shaped to fit over an end of a camera lens; a wiper movably attached to the housing, the wiper movable across the housing from a first position adjacent a first side of the housing to a second position adjacent a second side of the housing, the wiper including a wiper layer located towards a center of the wiper and along a length of the wiper, the wiper layer extending below the wiper, a first SMA wire layer located on a first side of the wiper layer along a length of the wiper, and a second SMA wire layer located on a second side of the wiper layer along a length of the wiper. When the first SMA wire layer is activated, the wiper is moved between the first position and the second position on the housing.

In one embodiment, the wiper further includes a first reinforcement layer located between the first SMA wire layer and the wiper layer and a second reinforcement layer located between the second SMA wire layer and the wiper layer. In another embodiment, the lens cleaning device further includes: a slide track located around a portion of the housing; a slide bar located on an end of the wiper and slidably engaged with the slide track. The slide bar slides along a length of the slide track when the wiper moves between the first position and the second position. In yet another embodiment, the lens cleaning device further includes: a first magnet proximate a first end of the slide track; and a second magnet proximate a second end of the slide track. The slide bar is formed of a ferrous material. The first magnet releasably anchors the wiper in the first position. The second magnet releasably anchors the wiper in the second position.

In one embodiment, when the wiper is in the first position and the second position, the wiper is substantially within a side edge of the housing such that the wiper does not substantially obstruct a field of view of the camera. In another embodiment, the housing further includes one or more gaps formed in sides of the housing such that debris swept by the wiper is evacuated from the housing. In yet another embodiment, the housing further includes a cover lens located on the housing. The wiper contacts the cover lens when the wiper moves between the first position and the second position. In one embodiment, the cover lens further includes a hydrophobic layer formed on an upper surface thereof.

In a third aspect, a lens cleaning device includes: a housing shaped to fit over an end of a camera lens; a wiper movably attached to the housing, the wiper movable across the housing from a first position adjacent a first side of the housing to a second position adjacent a second side of the housing; at least one SMA extending around at least a portion of the housing and into contact with the wiper; a bias spring located between the housing and the wiper for biasing the wiper towards one of the first position and the second position. When the SMA wire is activated, the wiper is moved between the first position and the second position of the housing such that the wiper sweeps debris from a field of view of the camera lens.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Figure 1:
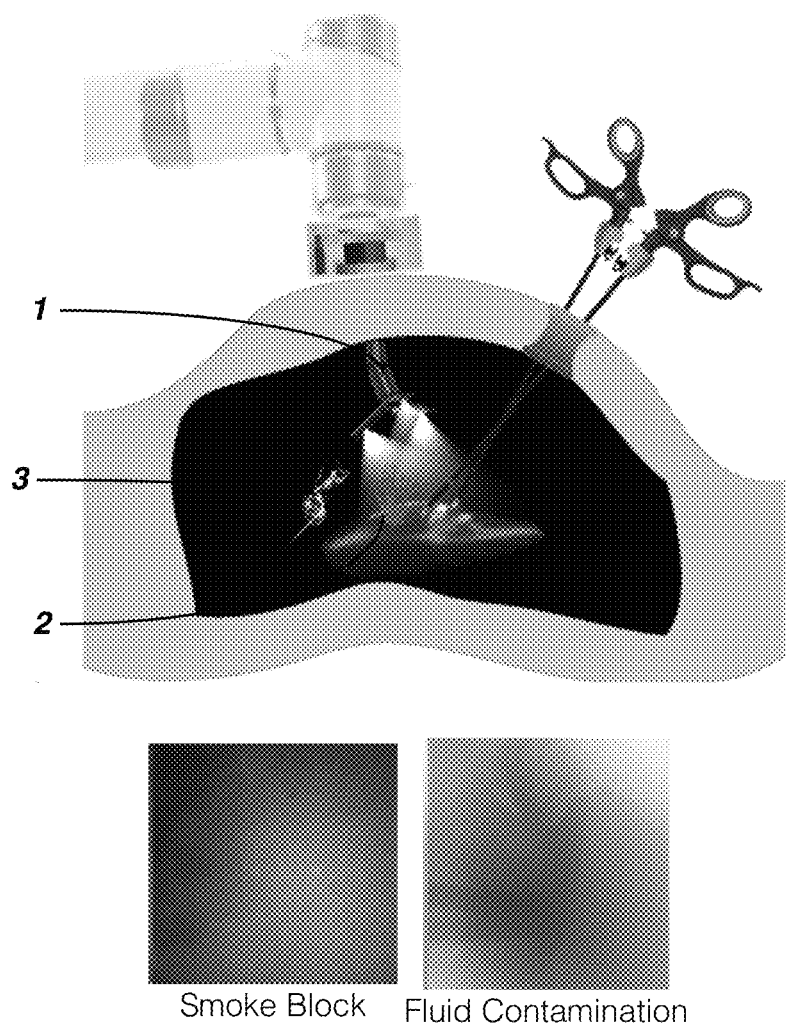
FIG. 1 shows an interior view of a laparoscopic camera and surgical tool according to one embodiment of the present disclosure.

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Embodiments described herein include a device that provides clear vision for in vivo robotic surgical cameras and that can actively prevent debris, evacuate smoke and clean a contaminated lens in a single module. A modular lens cleaning system for in vivo surgical cameras features minimal intraoperative interruption by maintaining clear visualization of a surgical field within a patient's anatomy. As illustrated in the exploded view of FIG. 2, embodiments include a sealing cover that can encompass a surgical camera's head. The modular lens cleaning system along with a surgical camera can enter the human body through dedicated/shared body incisions or natural orifices. During a surgical procedure, the modular lens cleaning system mimics mammalian eyelid blinking to actively wipe off contamination.

Embodiments of the lens cleaning device described herein utilize recent advances in soft robots and actuators, which adopt smart materials with compliance similar to soft biological muscles for improving safety of human-robot interaction. Embodiments provide new approaches that have great potential to facilitate the development of an effective miniature eyelid mechanism for this project. Soft actuators based on piezoelectric materials (PZTs), electroactive polymers (EAPs), or shape memory alloys (SMAs) suffer actuation performance trade-off between deformation, output forces, and actuation frequencies. Piezoelectric bending actuators feature highest actuation frequency at kHz scale, but are limited by their small deflections and light actuation force. Various types of EAP actuators including ionic polymer-metal composites (IPMC), carbon nanotubes (CNTs), and dielectric elastomers (DEAs) can achieve extremely large recoverable strains (40% 900%) and large output force. However, high voltages (>1 kV) are required to activate EAP actuators for obtaining such performance. SMA materials possess properties of high power-to-weight ratio, low driving voltages, 4% 8% recoverable strains, and great bio-compatibility, which attract vast attention of researchers to develop novel actuators in medical application. In comparison to PZT and EAP actuators, the main limitation of SMA actuators is their slow actuation frequencies that are affected by SMA materials' temperature rates for heating and cooling. Various SMA cooling methods based on forced heat convection have been investigated to expedite the actuation frequency. Embodiments described herein include a SMA bending-twisting actuator design for eyelid by employing antagonistic thin SMA wires attached on both sides of a soft composite to achieve high actuation frequency at least comparable to human eyes.

Figure 3:
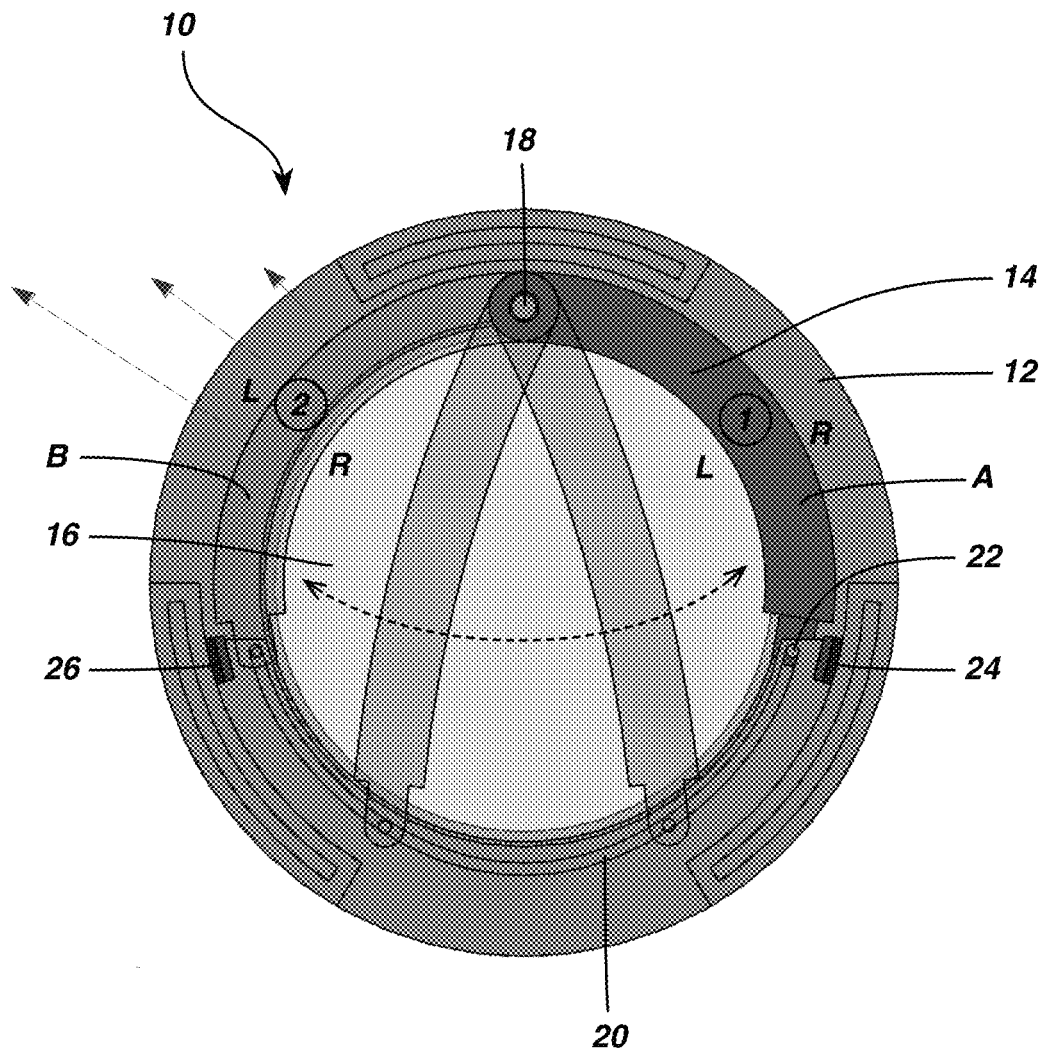
FIG. 3 shows a top view of a lens cleaning device including a wiper according to one embodiment of the present disclosure.

Referring to FIG. 3, a lens cleaning device 10 includes a housing 12 shaped to fit over the surgical scope camera 1 (FIG. 1). The lens cleaning device includes a wiper 14 movably mounted on the housing 12 and a cover lens 16 secured to the housing and shaped to fit over a lens of the surgical scope camera 1. The wiper 14 is attached to the housing 12 with a hinge 18 such that the wiper 14 pivots about a first end of the wiper 14 with respect to the housing 12. The housing 12 further includes a sliding track 20 located around the housing 12 adjacent a second end of the wiper 14. The second end of the wiper 14, which is distal from the hinge 18 and the first end of the wiper, is slidably engaged with the sliding track 20 such that the second end of the wiper 14 slides around the housing 12 as the wiper 14 pivots about the hinge 18. The second end of the wiper 14 may be slidably secured to the sliding track 20, such as with a sliding bar 22 located on the wiper 14 that fits within the sliding track 20. The sliding bar 22 is preferably formed of a ferrous metal material.

The housing 12 further preferably includes a first magnet 24 located at a first end of the sliding track 20 and a second magnet 26 located at a second end of the sliding track 20. The first magnet 24 anchors the wiper 14 in a first position A adjacent a first side of the housing 12 and the second magnet 26 anchors the wiper 14 in a second position B adjacent a second side of the housing 12 as shown in FIG. 3. When the wiper 14 is in the first position, the wiper 14 is positioned over the first side of the housing 12 such that the wiper 14 does not obstruct a view of the surgical scope camera 1 through the cover lens 16 and the housing 12. Similarly, when the wiper 14 is in the second position, the wiper 14 is positioned over the second side of the housing 12 such that the wiper 14 does not obstruct a view of the surgical scope camera 1 through the cover lens 16 and the housing 12.

Figure 4A:
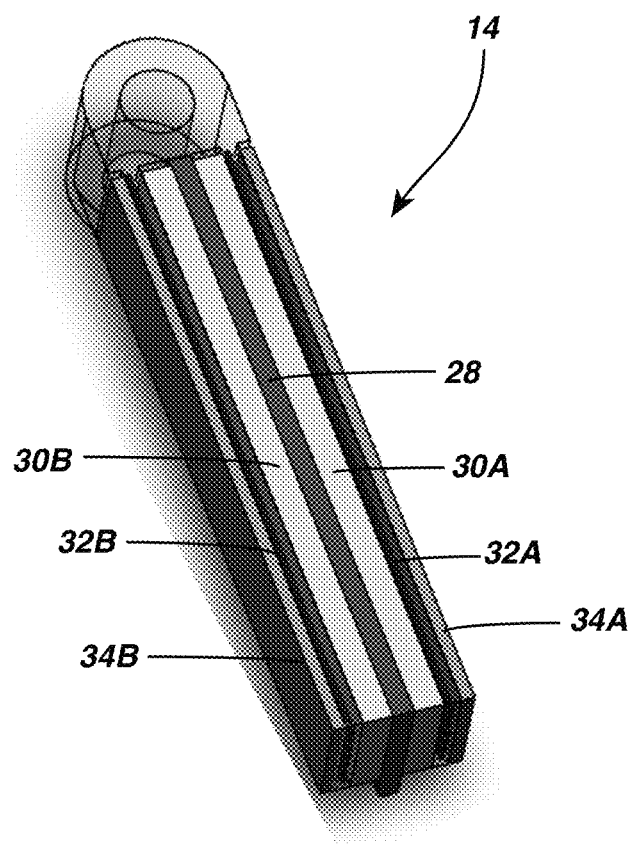
FIG. 4A shows a cross sectional top view of a wiper of a lens cleaning device according to one embodiment of the present disclosure.

Referring now to the cross-sectional view of FIG. 4A, the wiper 14 includes a plurality of layers, including a wiper layer 28, reinforcement layers 30A and 30B located on opposing sides of the wiper layer 28, SMA layers 32A and 32B, and coating layers 34A and 34B located over the SMA layers 32A and 321. The wiper layer 28 is preferably formed of polydimethylsiloxane (PDMS), which is a silicon-based polymer that is thermally stable and provides a low friction interaction with the cover lens 16. The reinforcement layers 30A and 301 are preferably formed of acrylonitrile butadiene styrene (ABS) and PDMS such that the wiper 14 has a stiffness that allows the wiper 14 to resiliently bend or deform as caused by the SMA layers 32A and 32B and described in greater detail below.

Figure 4B:
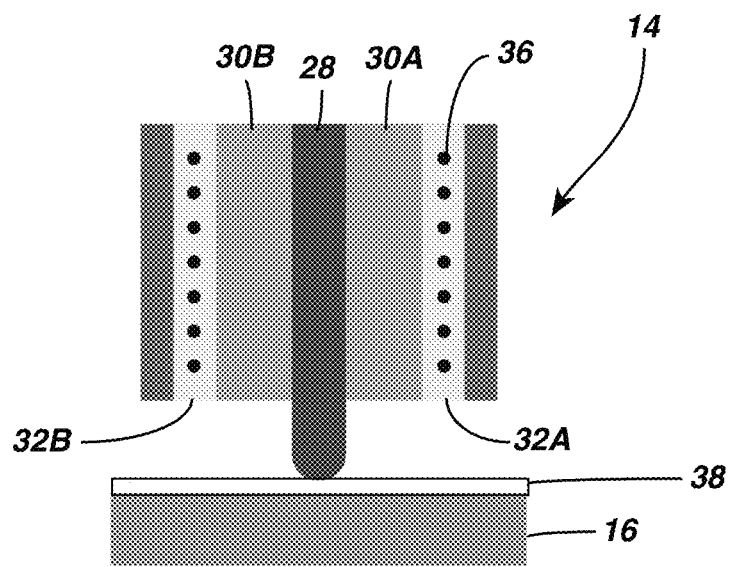
FIG. 4B shows a lengthwise cross sectional view of a wiper of a lens cleaning device according to one embodiment of the present disclosure.
Figure 4C:
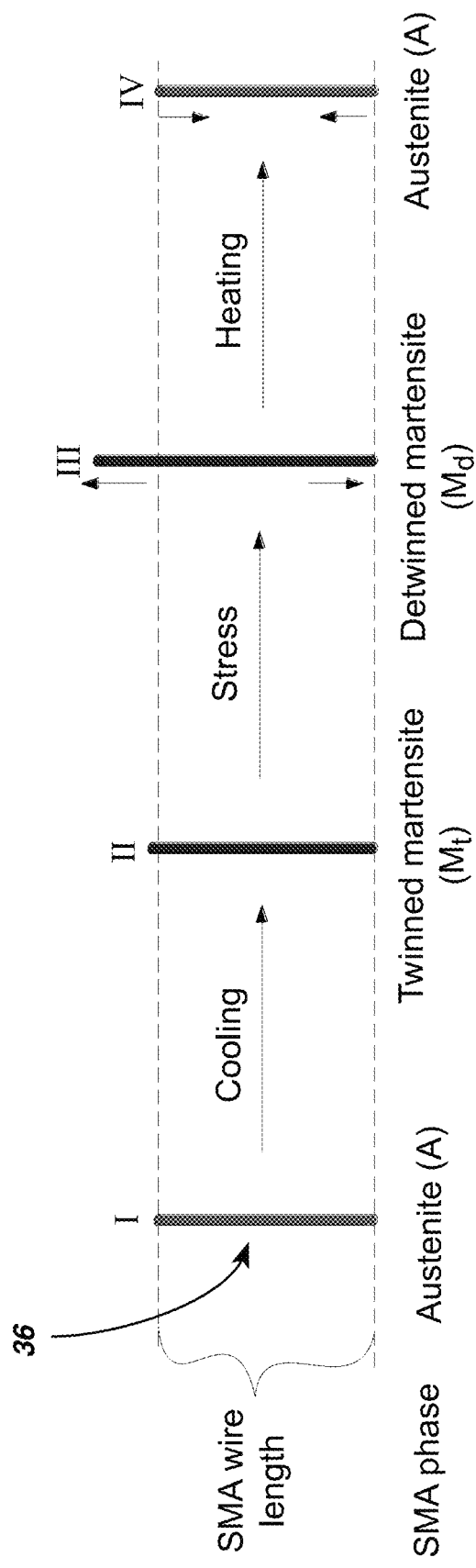
FIG. 4C shows a diagram of phase change of an SMA wire of a lens cleaning device according to one embodiment of the present disclosure.

Referring to FIG. 4B, which is a cross-sectional view along a length of the wiper 14, the SMA layers 32A and 32B include one or more SMA wires 36 embedded within opposing sides of the wiper 14 and along a length of the wiper 14. The one or more SMA wires 36 preferably have a diameter of from about 25 μm to about 80 μm. Deformation of the wiper 14 described herein is controlled by phase transformation of the one or more SMA wires 36, as shown in FIG. 4C. The one or more SMA wires 36 may be heated above an austenite finish temperature such that the one or more SMA wires 36 transforms to the phase of austenite (A) with a minimum wire length. When the one or more SMA wires 36 are cooled below a martensite finish temperature under zero-stress, the one or more SMA wires 36 transform to the phase of twinned martensite ($M_t$) without substantial change in length of the one or more SMA wires 36. Extension stress of the one or more SMA wires can elongate the one or more SMA wires from about 4% to about 8% of an original length of the one or more SMA wires 36. Extension stress further transforms the one or more SMA wires 36 into the phase of detwinned martensite ($M_d$). Upon heating the one or more SMA wires 36 when elongated, the one or more SMA wires 36 contract such that the one or more SMA wires 36 recover an original length as shown in FIG. 4C.

Referring again to FIG. 4B, the coating layers 34A and 34B preferably include a biocompatible hydrophobic and hydrophilic coating layer formed thereon. Similarly, the cover lens 16 preferably includes a biocompatible hydrophobic and hydrophilic coating layer 38 formed on the cover lens 16 to ensure effective contaminant removal from the cover lens 16 as described in greater detail below. As further shown in FIG. 4B, the wiper layer 28 preferably extends below the wiper 14 such that the wiper layer 28 contacts the cover lens 16 to remove any debris accumulated on the cover lens 16 when the wiper 14 is swept across the cover lens 16.

Referring again to FIG. 3, the wiper 14 swept across the cover lens 16 to any debris that has accumulated on the cover lens 16. The wiper 14 is configured to pivot about the hinge 18 such that the wiper 14 swings across the cover lens 16 from a first side of the housing 12 to a second side of the housing 12. The wiper 14 is further guided by the sliding track 20 with which an end of the wiper 14 is slidably engaged. A magnetic force between one of the first magnet 24 and the second magnet 26 and the sliding bar 22 secures the wiper 14 in a position such that the wiper 14 is within a first side or second side of the housing 12 when the SMA layers 32A and 32B are deactivated. When the wiper 14 is in position 1 of FIG. 3, the one or more SMA wires 36 on "L" and "R" sides of the wiper 14 are at the phases of M and M respectively. Movement of the wiper 14 from position 1 to position 2 occurs by activating the one or more SMA wires 36 on the "R" side of the wiper 14. Activation of the one or more SMA wires 36 on the "R" side of the wiper 14 causes the one or more SMA wires 36 on the "R" side to contract as a phase of the one or more SMA wires 36 on the "R" side goes from to A. Contraction of the one or more SMA wires 36 on the "R" side of the wiper 14 applies a distributed force on the wiper 14, which is substantially bent, such that a magnetic anchoring force of the first magnet 24 on the sliding bar 22 is broken and the wiper 14 subsequently move quickly to position 2. When the wiper 14 moves from position 1 to position 2, the one or more SMA wires 36 on the "L" side of the wiper 14 are passively stressed from $M_t$ to $M_d$. The wiper 14 may be subsequently moved from position 2 to position 1 by activating the one or more SMA wires 36 on the "L" side of the wiper 14.

Figure 5:
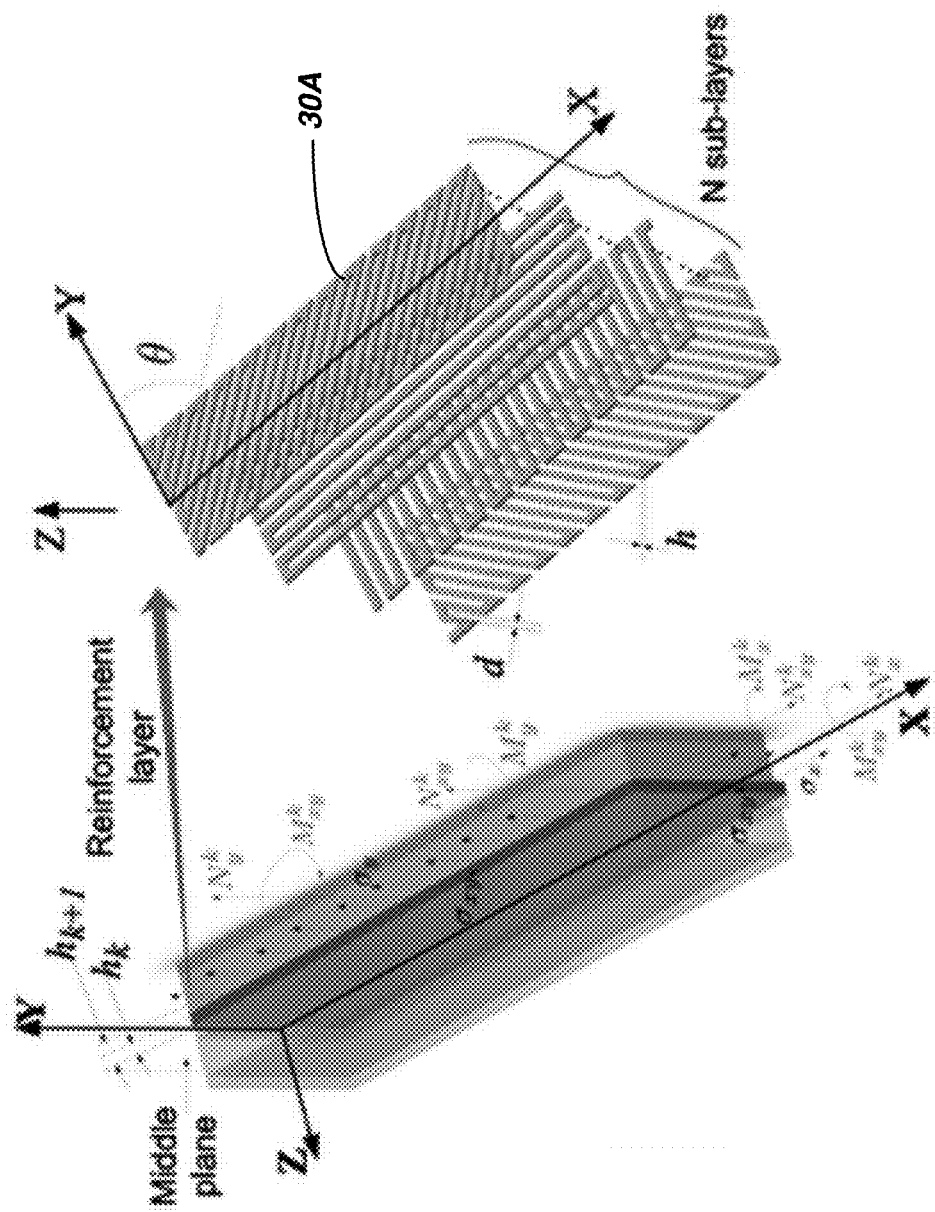
FIG. 5 shows a reinforcement layer and construction of a wiper of a lens cleaning device according to one embodiment of the present disclosure.
Figure 6:
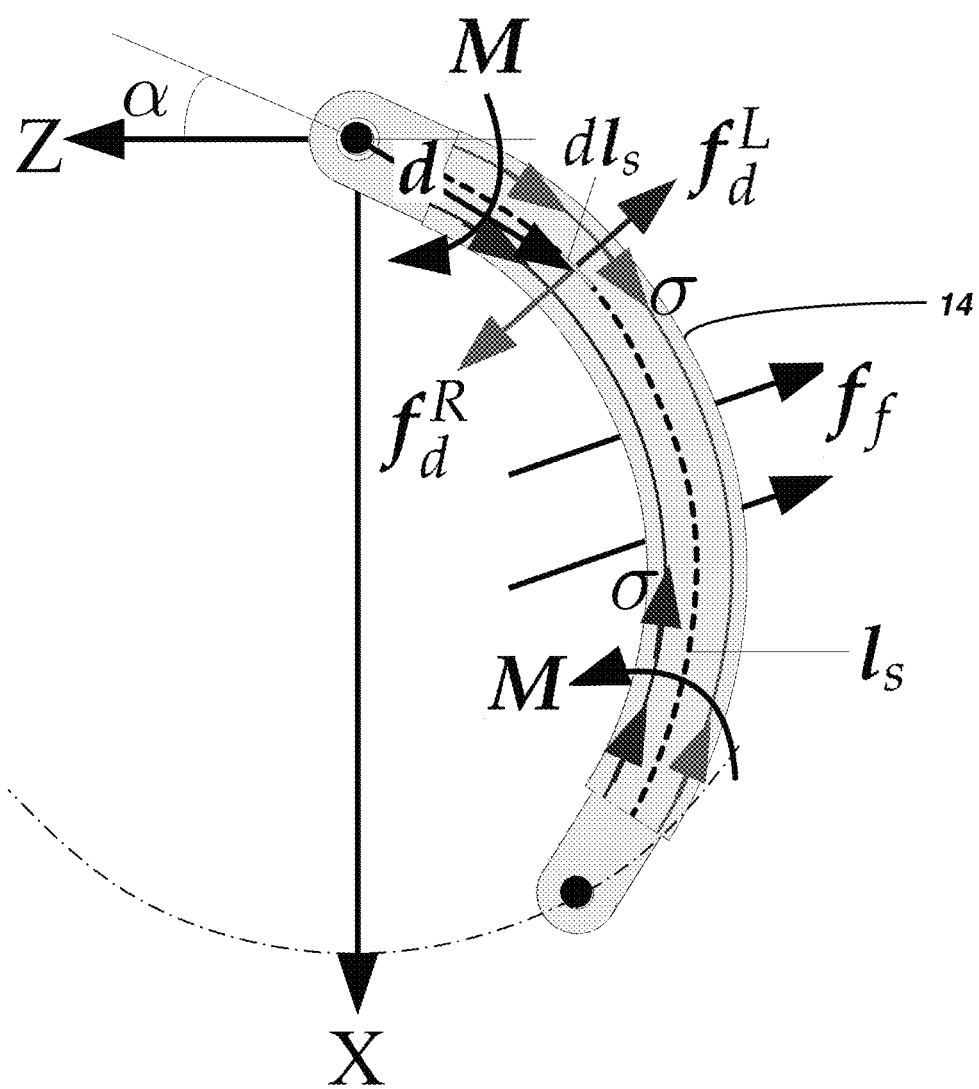
FIG. 6 shows a diagram of a wiper and motion of the wiper according to one embodiment of the present disclosure.

Movement of the wiper 14, including a bending modulus, may be determined based on pattern designs of layers of the wiper 14 and an actuation force distribution on the deformed wiper according to variations of arrays of SMA wires of the wiper 14. The wiper arm 14 is formed by stacking various laminas that feature different functionality. Stresses and moments acting on different layers may be defined by equivalent forces $N=[N_x, N_y, N_{xy}]T$ and moments $M=[M_x, M_y, M_{xy}]T$ at a middle plane X-Y, as shown in FIG. 5. A bending behavior of the wiper is determined as: $N=\Sigma_{k=1}^n N^k$, $M=\Sigma_{k=1}^H M^k$, where $N^k=[N_x^k,N_y^k,N_{xy}^k]=\int_{h_{k-1}}^{h_k}[\sigma_x,\sigma_y,\sigma_{xy}]_k^T dz$; $M^k=[M_x^k,M_y^k,M_{xy}^k]=\int_{h_{k-1}}^{h_k}[\sigma_x,\sigma_y,\sigma_{xy}]_k^T z\, dz$; $\sigma_x,\sigma_y,\sigma_{xy}$ are stresses per unit length on a kth layer; $h_k$ represents a distance between a middle plane and the far surface of the kth layer. Middle plane strains ($\epsilon=[\epsilon_x,\epsilon_y,\epsilon_{xy}]^T$) and curvatures ($\kappa=[\kappa_x,\kappa_y,\kappa_{xy}]^T$) are thus governed by $$\begin{bmatrix} N \\ M \end{bmatrix} = \begin{bmatrix} A & B \\ B & D \end{bmatrix}\begin{bmatrix} e \\ \kappa \end{bmatrix},$$

where A, B, D are stiffness matrices and defined by $A_{i,j}=\Sigma_{k=1}^n[Q_{i,j}]_k(h_k-h_{k-1})$, $B_{i,j}=(1/2)\Sigma_{k=1}^n[Q_{i,j}]_k(h_k^2-h_{k-1}^2)$, and $D_{i,j}=(1/3)\Sigma_{k=1}^n[Q_{i,j}]_k(h_k^3-h_{k-1}^3)$; i, j represent row and column numbers of the ABD matrix. A lamina stiffness matrix Q of the wiper 14 may be determined by a design of reinforcement layers 30A and 30B, as shown in FIG. 5. N sub-layers in the reinforcement layers 30A and 30B are varied by lamina thickness h, filament gap d, material types (ABS or PDMS), and ply orientation θ. An optimized sub-layer structural design is analyzed considering a wiping frictional force $f_f$, SMA array force $f_s$, and a magnet anchoring force $f_m$, as illustrated in FIG. 6.

Analysis of actuation of the wiper 14 includes modeling interactive forces/moments from SMA layers 32A and 32B, wiper bending and sweeping friction. The wiper 14 is preferably designed having sufficiently large axial stiffness Ea, it can be assumed that the wiper 14 bending around an X axis is negligible, as shown in FIG. 5, and thereby reducing an analysis from three dimensions to two dimensions in an XZ plane as shown in FIG. 6. Phase transformation of the SMA wires induces internal stresses s and applies forces normal to a central line of the wiper 14 for shape deformation. For SMA arrays with $N_s$ wires on "L" and "R" sides, an SMA distributed force $f_d^{L,R}$ on the wiper 14 can be formulated by $f_d^{L,R}=\Sigma_{i=1}^{N_s}d(\sigma_i S)/dI_s$, where S is the cross-sectional area of the SMA wire; $I_s$ denotes a deformed arc length along the wiper 14. Internal stress $s_i$ of SMA wires of the ith wire is determined by $\dot{\sigma}_i=D\dot{\epsilon}+\Omega\dot{\xi}+\Theta\dot{T}$, where $\epsilon$ is the wire strain; T is the SMA temperature; $\xi$ is the martensite fraction; $\Theta$ is the thermal expansion coefficient; D is the Young's modulus and C is the transformation tensor. Motion for the wiper 14 can be calculated as $dM/dI_s+d\times f_d^L+d\times f_d^R+d\times df_f/dI_s=\rho I\ddot{\alpha}$, where d is the location vector for computing resultant moments; $f_f$ is a friction force between the wiper 14 and the cover lens 16, ρ is a mass density of the wiper 14; I is a moment of inertial. A quasi-static condition makes the term for angular acceleration $\ddot{\alpha}$ equal to zero.

Figure 2:
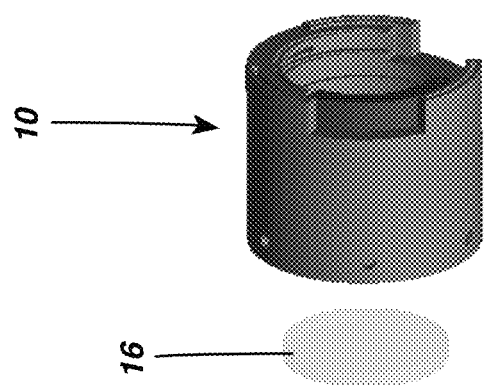
FIG. 2 shows an exploded view of a lens cleaning device according to one embodiment of the present disclosure.
Figure 2:
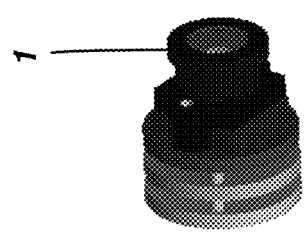
Figure 2:
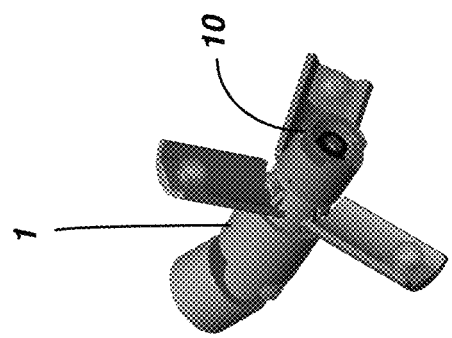
Figure 7:
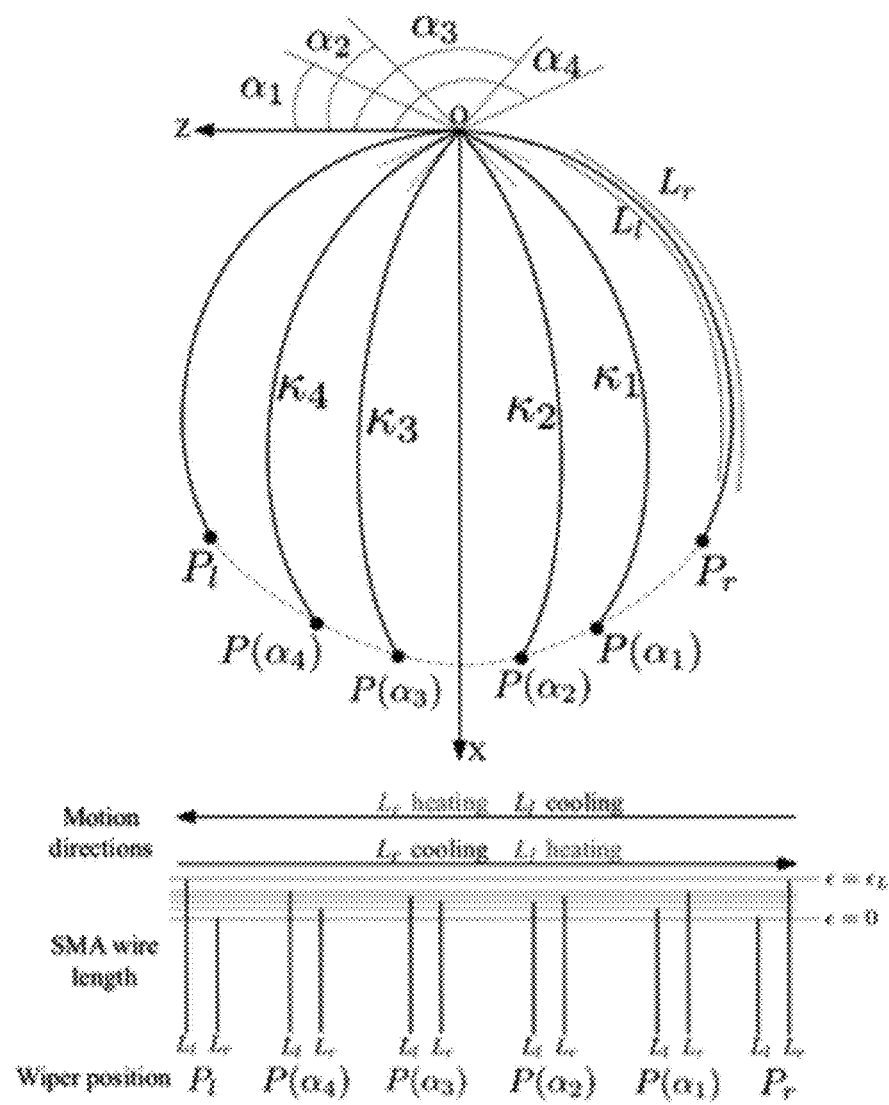
FIG. 7 shows a diagram of a position of a wiper and SMA wire strains during an actuation cycle according to one embodiment of the present disclosure.

An actuation frequency of the wiper 14 is defined by a number of actuation cycles (movement of the wiper 1 from position 1, to position 2, back to position 1 as shown in FIG. 2) per second. An actuation frequency is directly related to a speed of phase transformation ($M_d$ to A) of the one or more SMA wires 36. As illustrated in FIG. 7, a mapping can may be established between a position of the wiper 14 P(α) and its bending curvature $k_i$. The bending curvature $k_i$ is controlled by the SMA wire lengths $L_l$, $L_r$ on both sides of the wiper.

A strain rate of an SMA wire is determined by a cycle of material phase transformation, which is governed by $\dot{\sigma}=D\dot{\epsilon}+\Omega\dot{\xi}+\Theta\dot{T}$ (the term $\Theta\dot{T}$ is ignorable due to the small value of $\Theta$). Martensite fraction $\xi$ that characterizes phase transformation kinetics can be modeled as a function of (σ,T) and formulated as $\xi=f_\xi(\sigma,T)$. If a stress strain relationship can be defined as $\sigma=f_o(\epsilon)$, the constitutive equation is reformulated as a first order nonlinear differential equation $f_o'(\epsilon)=D\dot{\epsilon}+\Omega f_\xi'(f_o'(\epsilon),T)$, which involves variables of $\epsilon$, $\dot{\epsilon}$, T, and $\dot{T}$.

An actuation frequency of the wiper 14 can thus be estimated by solving e and T during wiping cycles. From a perspective of energy balance for SMA wires, a rate of heat flow is approximately equal to a rate of energy change when a ration of wire length and diameter is sufficiently large (biot number $B_i$<0.1). A heat transfer equation of an SMA wire may be formulated by $mc_p\dot{T}=m\Delta h\dot{\xi}=I^2R(\xi)-hS_a(T-T_\infty)$, where m is wire mass, $c_p$ is specific heat in constant pressure; Dh is the latent heat of transformation; $S_a$ is the surface area of the SMA wire; h is the heat convection coefficient; I is the input current; $R(\xi)$ is the electrical resistance; and $T_\infty$ is the ambient temperature. By substituting the functions of $\xi=f_\xi(\sigma,T)$ and $\sigma=f_o(\epsilon)$ into the heat transfer function, another set of first order differential equation with variables of e, $\epsilon$, $\dot{\epsilon}$, T and $\dot{T}$ can be obtained to pair with the constitutive equation for solving the strain rate of an SMA wire.

Factors that may affect resultant strain rate and subsequently affect an actuation frequency f of the wiper 14 are bias stress $\sigma_b$, heat convection coefficient h, and Joule heating strategy I of the SMA wire arrays. A relatively large bias stress can significantly accelerate phase transformation of a deactivated SMA wire array. Influential parameters bias stress involve a bending curvature k of the wiper, bending stiffness $E_b$, the bias stress from the activated SMA wire array $s_u$, the wiper-lens frictional force $f_f$, and magnetic anchoring force $f_m$. A larger h can result in faster SMA phase transformation from A to $M_d$. The heat convection coefficient h can be modeled by the speed of active air flow v, the SMA wire diameter d and air flow distribution according to the forced convection theory.

To enable fast phase transformation without applying excessive heat that would damage SMA wires, simultaneous acquisition of a rotation angle of the wiper 14 and temperatures of the SMA wire arrays during motion is required. Methods including sensor-based and non-sensor based acquisition of the rotation angle may be applied. In a sensor-based method a micro-thermal sensor is integrated in the wiper 14 to measure a temperature of the SMA wires. A rotational angle of the wiper 14 may be captured by a camera imaging system and processed by imaging-based methods. In a non-sensor based method, electrical resistance of the SMA wire is measured to estimate wire temperature.

Figure 8A:
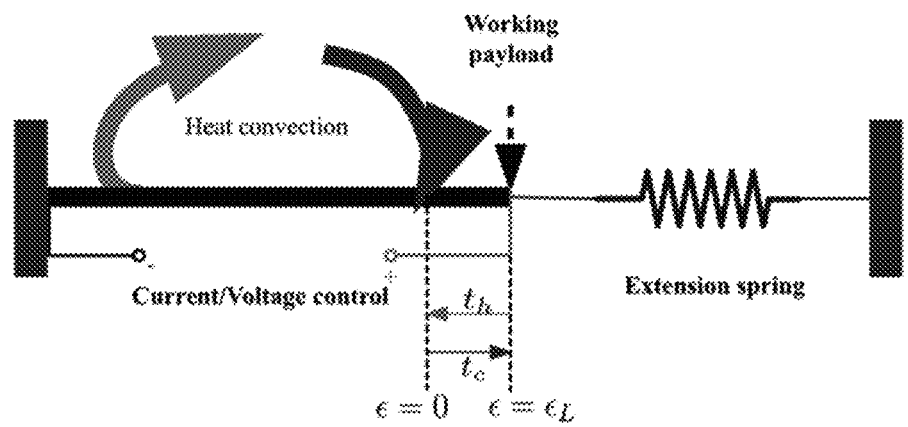
FIG. 8A shows a diagram of an SMA actuator having an extension spring as a bias load according to one embodiment of the present disclosure.
Figure 8B:
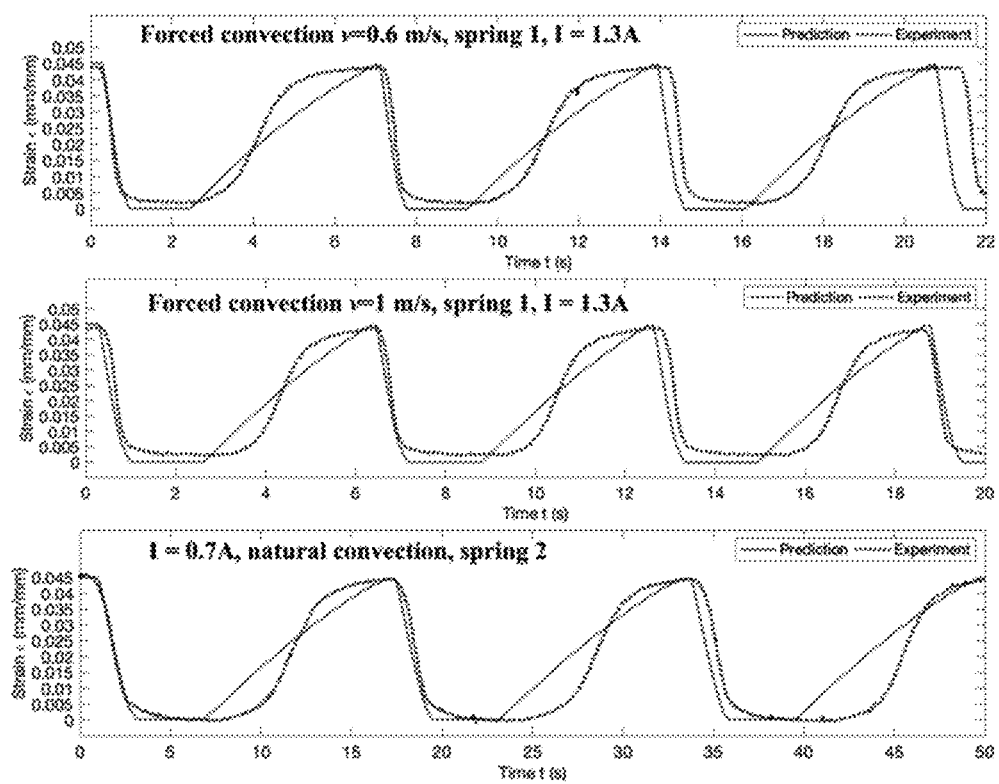
FIG. 8B shows a chart of predicted and measured strain cycles of an SMA actuator according to one embodiment of the present disclosure.

In one exemplary study, feasibility of embodiments described herein is demonstrated for a simple one-dimensional SMA actuator with extension spring and bias load as shown in FIG. 8A. A strain cycle of an actuator as shown includes a heating period $t_h$ and a cooling period $t_c$. During a heating period, Joule heating is applied to the SMA wire to activate internal energy of the wire for enabling contraction of the wire at (at the phase of A).

Figure 9A:
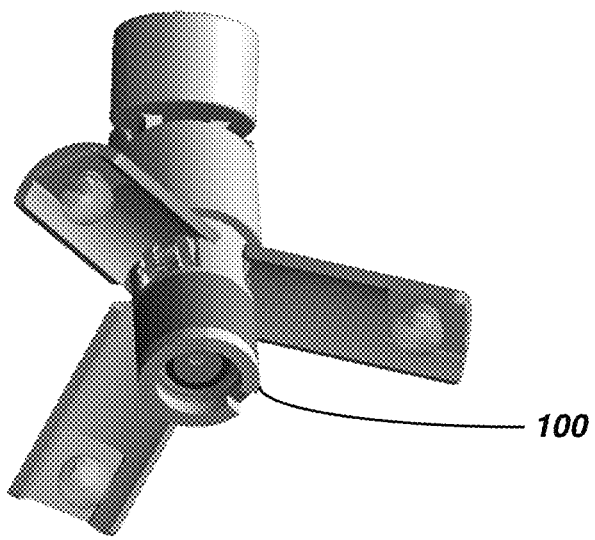
FIG. 9A shows a laporoscopic camera and lens cleaning device secured thereto according to one embodiment of the present disclosure.
Figure 9B:
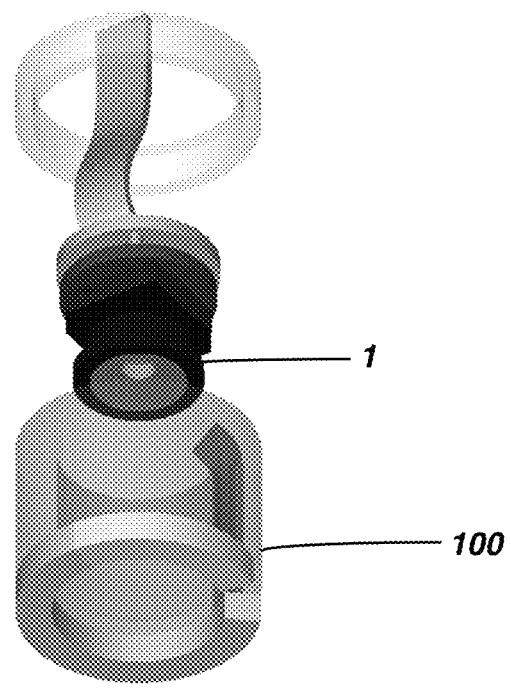
FIG. 9B shows an exploded view of a laporoscopic camera and lens cleaning device according to one embodiment of the present disclosure.
Figure 9C:
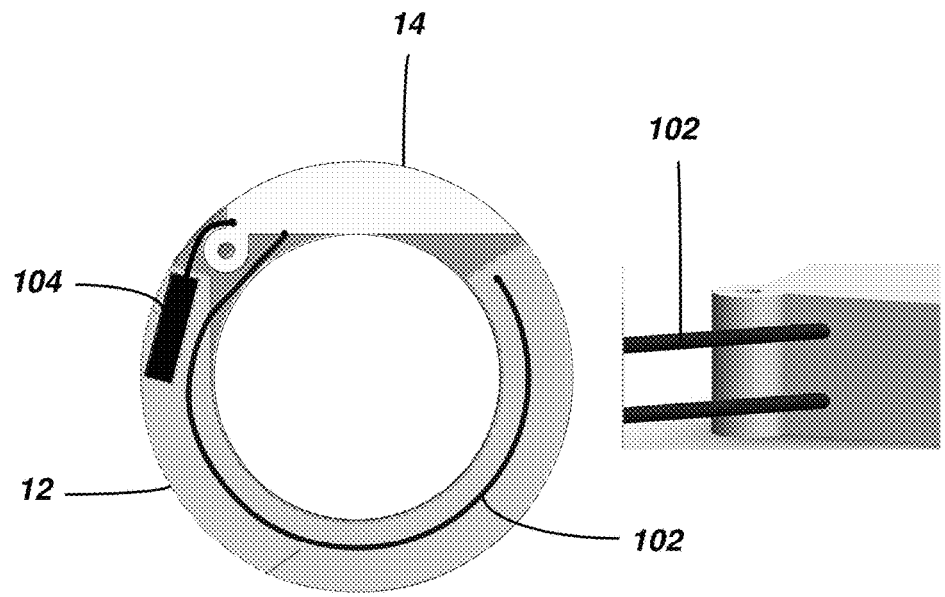
FIG. 9C shows a top view of a lens cleaning device according to one embodiment of the present disclosure.
Figure 9D:
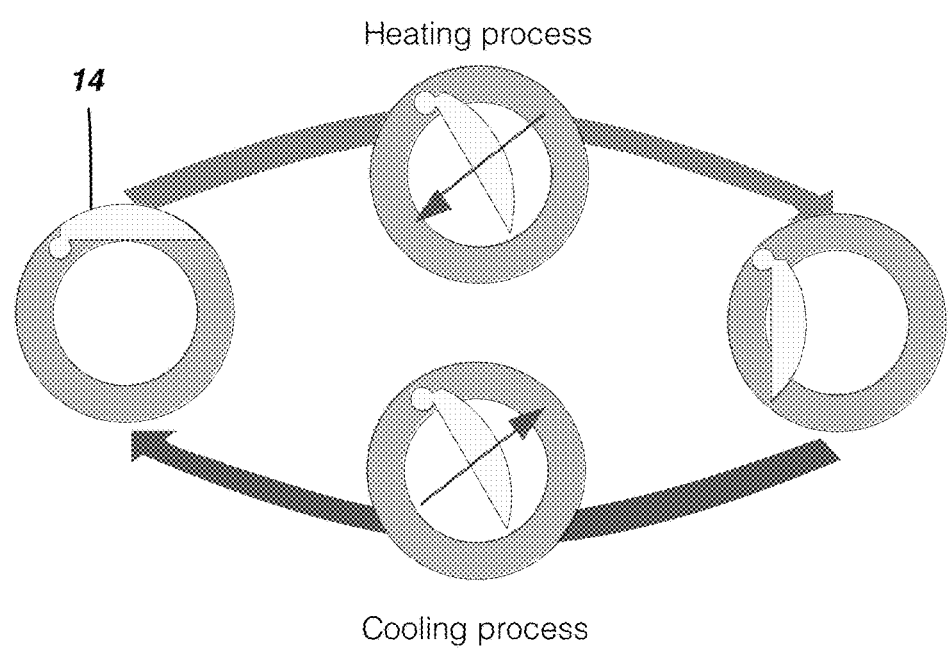
FIG. 9D shows actuation of a wiper on a lens cleaning device according to one embodiment of the present disclosure.

Referring to FIGS. 9A-9D, in another embodiment, a modular lens cleaning device 100 is connected with N paralleled SMA wires 102 that are embedded in a circular edge of the module. A bias load connects to the wiper 14 on an outer side of the hinge 18 and provides force to reset the wiper's position after being actuated by the SMA wires. FIG. 9D demonstrates a full actuation cycle of a wiper 14, wherein in a heating process the SMA wires transform from $M_d$ to A, thereby resulting in contractive deformation of the wires thereby resulting in the wiper 14 sweeping across the cover lens 16. In a cooling process, the SMA wires are tensioned by the bias load and transform from A to $M_d$. A bias load may come with various types, such as a constant force spring, extension spring, magnet, or another set of SMA wires. In a preferably embodiment, a micro extension spring is employed as a bias load for the modular lens cleaning device 100.

FIG. 10A shows an embodiment of the lens cleaning device 100 including the wiper 14 and an extension spring 104 secured to the housing 12 at a first end and to the wiper 14 at a second end of the extension spring 104. The SMA wires 102 are located around an edge of the housing 12 of the modular lens cleaning device 100 and extend into the wiper 14, as shown in FIGS. 10A and 10B. As shown in FIG. 9D, during an actuation cycle of the modular lens cleaning device 100 the SMA wires 102 transform from $M_d$ to A, which results in contractive deformation of the SMA wires 102 and consequently moves the wiper 14 to sweep across the cover lens 16. During a cooling process, the SMA wires 103 are tensioned by the extension spring 104 and transform from A to $M_d$, thereby allowing the wiper 14 to move back across the cover lens 16 to a starting position.

Actuation of the wiper 14 involves the torques of $\tau_\omega=\hat{F}_\omega r_1$ from the SMA wires, $\tau_s=F_s r_2$ from the micro extension spring, and $\tau_f=F_f r_3$ from the friction between the wiper and the cover lens, as shown in FIG. 10B. By assuming that the actuation mechanism works in a quasi-static manner, the heating and cooling processes are governed by the equation below, and illustrated in FIG. 10C.

$$\underbrace{\frac{r_1}{r_2}\hat{F}_w^h - \frac{r_3}{r_2}F_f = F_s}_{F_G \text{ in Heating}}, \underbrace{\frac{r_1}{r_2}\hat{F}_w^c + \frac{r_3}{r_2}F_f = F_s}_{F_L \text{ in Cooling}}, \quad (1)$$

here $\hat{F}_\omega^h$ and $\hat{F}_\omega^h$ are effective SMA forces during heating and cooling processes respectively; $F_f=\mu F_N$; $\mu$; $\mu$ denotes frictional coefficient between the wiper and the cover lens; $F_N$ is the applied force on the cover lens from the wiper. If the bounds of the actuation forces $F_U$ and $F_I$ can be calculated for the spring force $F_s\epsilon[F_L,F_U]$ which is a function of the wiper's 14 rotational angle $\theta$ and modeled in the equation below, the spring rate k and the initial tension $F_I$ of an extension spring can be selected accordingly. $\Delta L$ represents the length deformation when $\theta=\pi/2$.

$$F_s(\theta) = k\left(r_2\left(\frac{\pi}{2} - \theta\right) + \Delta L\right) + F_s, \quad (2)$$

An effective force $\hat{F}_\omega$ from the SMA wires 102 is modeled as $$\hat{F}_w = N\sigma S_c \cos\left(\frac{\theta}{2}\right) \quad (3)$$

where N is the number of SMA wires that drive the wiper; $\sigma$ and $S_c=\pi(d/2)^2$ denote the wires' internal stress and cross sectional area. d represents the wire diameter. According to (1), the bound of $F_s$ can be determined by $\hat{F}_\omega^h$ using and $\hat{F}_\omega^c$. The SMA wire stress a is the key variable in $\hat{F}_\omega$. The boundary values of a are needed to determine $F_U$ and $F_L$ for the heating and cooling processes.

Figure 10:
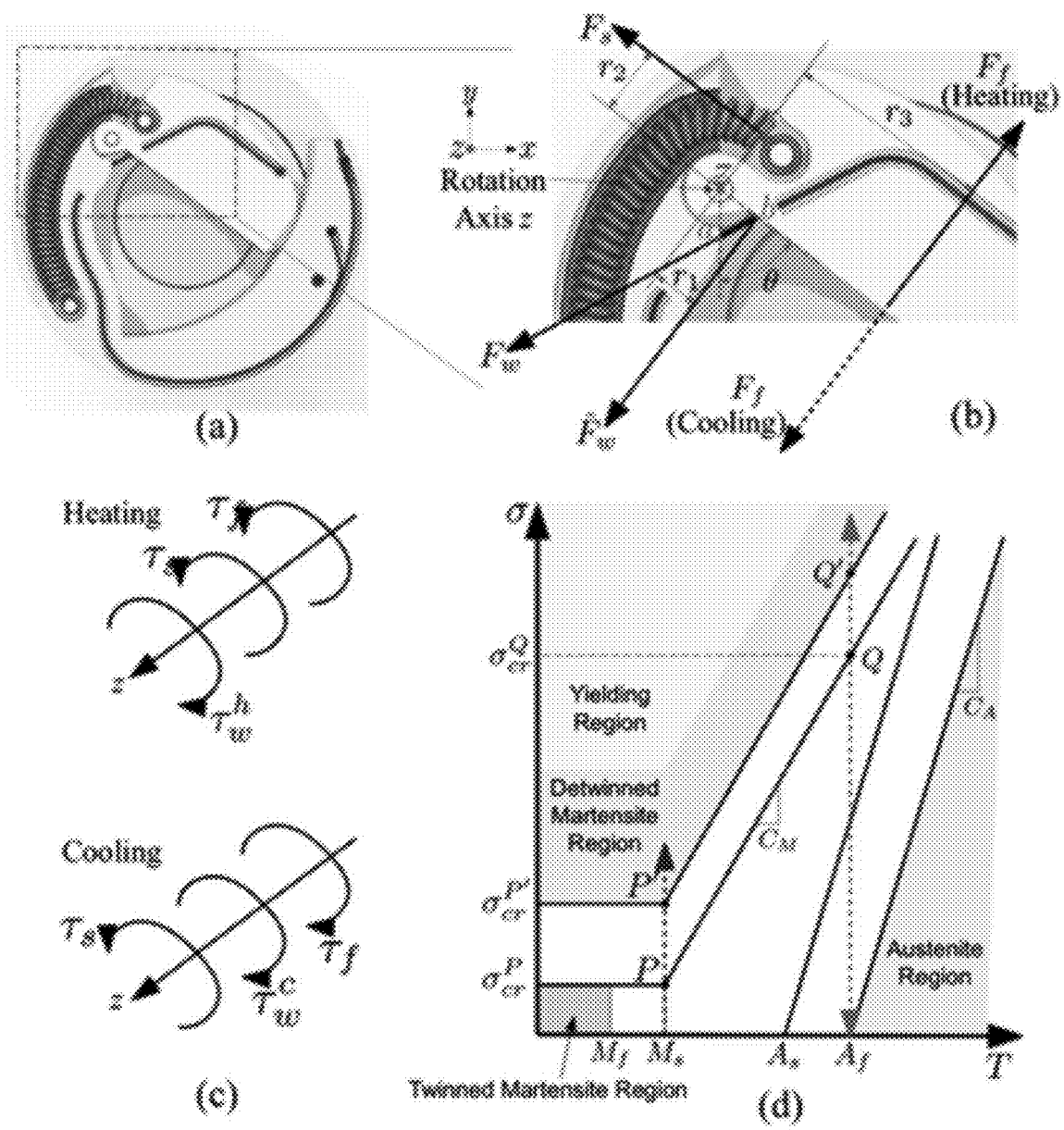
FIG. 10 shows analysis of actuation of a wiper of a lens cleaning device according to one embodiment of the present disclosure.

FIG. 10($d$) shows a critical stress model of one-dimensional SMAs for phase transformation (26). The $\sigma$-T graph indicates that it requires increasing applied stresses for SMA wires 102 to transform to $M_d$ when $T>M_s$, and nearly constant applied stress for SMA wires 102 to transform to $M_d$ when $T<M_s$. In the heating process, when $T=A_f$ (the austenite finish temperature under zero stress), the SMA wires exhibits the property of superelasticity shown in the red arrows. When the bias stress increases above $\sigma_{cr}^Q$, the SMA wires will start to be elongated and fail in actuating the wiper. In the cooling process, when the SMA wires cools down to $T=M_s$, (the martensite start temperature under zero stress), the bias stress needs to provide at least $\sigma_{cr}^{P'}$ on the SMA wires in addition to overcome the friction for resetting the wiper to its initial position. The critical stress $\sigma_{cr}^Q$ can be calculated by $$\sigma_{cr}^Q = \sigma_{cr}^P + C_M(A_f - M_s), \tag{4}$$

where $\sigma_{cr}^P$, $C_M$, $A_f$, $M_s$, and $\sigma_{cr}^{P'}$ are all material-related parameters. $\sigma_{cr}^Q$ and $\sigma_{cr}^{P'}$ can be used to determine $\hat{F}_\omega^h$ and $\hat{F}_\omega^c$ respectively according to (3).

A full actuation cycle (or strain cycle) time of the wiper 14 adds up durations of the heating process $t_h$ and the cooling process $t_c$, as shown in FIG. 9D. The strain $\varepsilon$ of one SMA wire is represented by $\varepsilon = L_{ab}/L$, where $L_{ab}$ is the length between the points a and b in FIG. 10B; and L denotes the length of the SMA wire. The strain $\varepsilon$ continuously changes between 0 (when $\Theta=0$) and $\varepsilon_L$ (when $\Theta=\pi/2$) in each cycle.

The strain rate $\dot\varepsilon$ of an SMA wire is determined by the cycle time of material phase transformation, which is governed by the one-dimensional constitutive equation of SMAs (26)

$$\dot\sigma = D\dot\varepsilon + \Omega\dot\xi + \tau\dot T, \tag{5}$$

where D is the Young's modulus; $\Omega$ is transformation tensor; $\varepsilon$ is the wire strain; $\xi$ is martensite fraction; $\tau$ is the thermal expansion coefficient; and T is the wire temperature. The term $\tau\dot T$ is ignorable due to the small value of $\tau$. The martensite fraction $\xi$ that characterizes the phase transformation kinetics can be modeled as $\xi_h = f_{\xi_h}(\sigma_h, T)$ for $M_d \to A$ and $\xi_c = f_{\xi_c}(\sigma_c, T)$ for $A \to M_d$ in (6) and (7)

$$\xi_h = \frac{1}{2}\cos\left\{a_A\left(T - A_s - \frac{\sigma}{C_A}\right)\right\} + \frac{1}{2}, \tag{6}$$

$$\xi_c = \frac{1}{2}\cos\{a_M[\sigma - \sigma_{cr}^{P'} - C_M(T - M_s)]\} + \frac{1}{2}, \tag{7}$$

where $a_A = \pi/(\sigma_{cr}^P - \sigma_{cr}^{P'})$ and $a_M = \pi/(A_f - A_s)$. According to (1), (3) and the system configuration in FIG. 10B, $\sigma$ can be modeled as $\sigma_h = f_{\sigma_h}(\varepsilon)$ for $M_d \to A$, and $\sigma_c = f_{\sigma_c}(\varepsilon)$ for $A \to M_d$. By taking the derivative of $\sigma$ and $\xi$ in respect to time t and substituting $\dot\sigma$; $\dot\xi$ in (5), the constitutive equation is reformulated as a first order differential equation with variables $\varepsilon$ and T $$f_{\sigma_\square}'(\varepsilon', \varepsilon) = D\dot\varepsilon + \Omega f_{\xi_\square}'(f_{\sigma_\square}(\varepsilon), f_{\sigma_\square}'(\varepsilon', \varepsilon), T, \dot T) \tag{8}$$

where the subscript $\square$ denotes h for the heating process and c for the cooling process.

To solve the strain cycle time, another set of $\varepsilon$–T relation is required. From the perspective of energy balance for SMA wires, the rate of heat flow is approximately equal to the rate of energy change when the ratio of wire length and diameter is sufficiently large (biot number $B_j < 0.1$) (27). Thus, the heat transfer equation of an SMA wire can be formulated by $$mc_p\dot T - m\Delta h\dot\xi_\square = I^2 R + \dot E, \tag{9}$$

where m is the wire mass; $c_p$ is specific heat in constant pressure; $\Delta h$ is the latent heat of transformation; I is the input current and equals to zero during the cooling process; R is the electrical resistance; and E represents the heat energy in the SMA wire.

In many applications, SMA wires are exposed in the air or submerged in heat dissipation liquids, which enable $\dot E$ to be formulated by directly using the heat convection model. However, the SMA wires in embodiments of the present disclosure are embedded in the housing 12, which may be formed of aluminum. The heat energy of the SMA wires will flow into the structure by conduction, and then go into the surrounding air by convection. To eliminate the air layer between the SMA wire and the aluminum structure, thermal grease is employed to fill the air gap. When the thickness of the thermal grease is small enough, the conduction term for such a layer is negligible. The thickness of the thermal grease layer is about 10. This value is far less than the thickness of the aluminum structure $\Delta r$ (see Table II). Therefore, $\dot E$ is modeled based on these two steps. The thermal energy in the SMA wires equals to the amount of heat energy transferred from the surrounding structure to the wires by heat conduction.

$$\dot E = k_a S_a \frac{T_a - T}{\Delta r}, \tag{10}$$

where $k_a$ is the thermal conductivity of the structure; $S_a$ is the surface area of the SMA wire; $\Delta r$ represents the distance between the center of SMA wires and the equivalent middle circle of the surrounding structure; and $T_a$ is the surrounding structure temperature.

The thermal energy stored in the surrounding structure equals to the amount of conductive heat from the SMA wires plus the amount of heat transfer by convection from the surrounding environment.

$$m_a c_{p_a} \cdot \dot T_a = -k_a S_a \frac{T_a - T}{\Delta r} - h S_b (T_a - T_\infty), \tag{11}$$

where $m_a$ is the structure mass; $c_{p_a}$ is the structure specific heat; h is the heat convection coefficient; $S_b$ represents the area of the structure surface in contact with the surrounding air; and $T_\infty$ is the ambient temperature.

By substituting $\dot\xi_\square = f_{\xi_\square}'(f_{\sigma_\square}(\varepsilon), f_{\sigma_\square}'(\varepsilon', \varepsilon), T, \dot T)$ in (9), the extra $\varepsilon$–T relation in the form of first order differential equation can be derived. The unknown parameter $T_a$ in (9) can be simultaneously solved by (11).

By combining (1), (2), and (3), the relations of $\sigma$ and $\Theta$ for the heating and cooling processes are obtained. To formulate $\sigma_\square = f_{\sigma_\square}(\varepsilon)$, $\Theta$ is to be replaced with $\varepsilon$. $\Theta$ and $\cos(\Theta/2)$ in (2) and (3) can be formulated as functions of $\varepsilon$ by using the law of cosines $$\Theta = \arccos\left(\frac{L_{za}^2 + L_{zb}^2 - \varepsilon^2 L^2}{2 L_{za} L_{zb}}\right), \tag{12}$$

$$\cos\left(\frac{\Theta}{2}\right) = \sqrt{\frac{1}{2} + \frac{L_{za}^2 + L_{zb}^2 - \varepsilon^2 L^2}{4 L_{za} L_{zb}}}, \tag{13}$$

where $L_{za}$ and $L_{zb}$ are the lengths of z-a and z-b, as shown in FIG. 10B. However, considering that $\sigma_\square = f_{\sigma_\square}(\varepsilon)$ and $\sigma_\square = f_{\sigma_\square}'(\varepsilon', \varepsilon)$ will be used in (8) and (9), the nonlinearity of (12) and (13) can significantly increase the complexity of (8) and (9) that leads to uncoverged numerical computation for $\varepsilon$ and T. To address this problem, we employ second and third degree polynomial functions to reformulate (12) and (13) for reducing their nonlinearity in (14) and (15)

$$\Theta(\varepsilon) = \sum_{m=1}^{3} p_m \varepsilon^{3-m}, \quad (14)$$

$$\cos\left(\frac{\Theta}{2}\right) = \sum_{n=1}^{4} q_n \varepsilon^{4-n}, \quad (15)$$

where $p_m$ and $q_n$ (m=1, 2, 3, n=1, 2, 3, 4) are polynomial coefficients. $\sigma_\square = f_{\sigma_\square}(\varepsilon)$ can thus be formulated by using (1), (2), (3), (14), and (15) as $$\sigma_\square = f_{\sigma_\square}(\varepsilon) = \frac{G - kr_2^2 \sum_{m=1}^{3} p_m \varepsilon^{3-m} + \hat{r}_3 F_f}{r_1 N S_a \sum_{n=1}^{4} q_n \varepsilon^{4-n}}, \quad (16)$$

where $G = \pi k r_2^2/2 + k r_2 \Delta L + r_2 F_i$; $\hat{F}_f = F_f$ in the heating process and $\hat{F}_f = -F_f$ in the cooling process. The derivative of $\sigma$ in (16) is defined as $$\sigma_\square = g_\square(\varepsilon)\dot{\varepsilon}, \quad (17)$$

where $g_\square(\varepsilon)$ represents a function of $\varepsilon$.

The rate forms of $\xi$ in (6) and (7) are derived as functions of $\varepsilon$ and $T$ by using (16) and (17), and represented by $$\dot{\xi}_\square = w_\square(\varepsilon, T)\dot{T} - u_\square(\varepsilon, T)\dot{\varepsilon}, \quad (18)$$

where $$w_h = -\frac{a_A}{2} \sin\left[a_A(T - A_s) - \frac{a_A}{C_A}\sigma_h(\varepsilon)\right], \quad (19)$$

$$w_c = \frac{a_M C_M}{2} \sin\{a_M[\sigma_c(\varepsilon) - \sigma_{cr}^{P'} - C_M(T - M_s)]\}, \quad (20)$$

$$u_h = -\frac{a_A g_h(\varepsilon)}{2C_A} \sin\left[a_A(T - A_s) - \frac{a_A}{C_A}\sigma_h(\varepsilon)\right], \quad (21)$$

$$u_c = \frac{a_M g_c(\varepsilon)}{2} \sin\{a_M[\sigma_c(\varepsilon) - \sigma_{cr}^{P} - C_M(T - M_s)]\}. \quad (22)$$

By substituting (18) and (17) for $\xi$ and/or $\sigma$ in (8) and (9), $\varepsilon$ and $T$ are formulated as functions of $\varepsilon$ and $T$ in ( ) and ( ) with ( ) for solving $T_a$ $$\dot{\varepsilon} = \frac{\Omega w_\square (I^2 R + k_a S_a (T_a - T)/\Delta r)}{(mc_p - m\Delta h w_\square)(g_\square - D + \Omega u_\square) + m\Delta h \Omega w_\square u_\square}, \quad (23)$$

$$\dot{T} = \frac{(g_\square - D + \Omega u_\square)(I^2 R + k_a S_a (T_a - T)/\Delta r)}{(mc_p - m\Delta h w_\square)(g_\square - D + \Omega u_\square) + m\Delta h \Omega w_\square u_\square}, \quad (24)$$

$$\dot{T}_a = \frac{-(k_a S_a + h S_b \Delta r) T_a + (k_a S_a T + h \Delta r S_b T_\infty)}{m_a c_{P_a} \Delta r}. \quad (25)$$

The numerical computation of $\varepsilon(t)$ and $T(t)$ involves determinating design parameters and initial conditions, and employing an effective numerical solver. The SMA property parameters including $M_f, M_s, A_s, A_f, C_M, C_A, c_p, h, D, \Omega$, etc., are provided by materials' datasheet or can be determined by running a set of testing experiments for the selected SMA wires. Compatible extension spring parameters $k, F_i$ are obtained according to embodiments herein. The proposed strain cycle model in ( ), ( ) and ( ) can be treated as initial value problem (IVP) with initial conditions of $\varepsilon_0 = \varepsilon_L$ and $T = T_\infty$. Considering the nonlinearity of ( ), ( ), and ( ), the fourth-order Runge-Kutta method (28) is employed as the numerical solver to approximate the solution of $\varepsilon(t)$ and $T(t)$. The computed strain cycle is used to identify the actuation frequency of the eyelid wiper mechanism, and to optimize the design parameters for achieving faster actuation speeds.

The modular lens cleaning device 100 is preferably integrated into an insertable robotic camera for surgical procedures. In a first example, a modular lens cleaning device includes spring rates k and initial tensions $F_i$ of micro extension springs for effective actuation of the wiper 14 according to the quasi-static analysis developed above. Actuation cycles of the wiper 14 are numerically computed based on various configurations of SMA wires 102 and extension springs 104. Contaminant removal efficiency of the vClear system is evaluated by using the conditions of fogging, bone dusts, and blood.

TABLE 1

Material Properties and Design Dimensions

| 2 Parameters | Value |
| --- | --- |
| Martensite finish temperature $M_f$ (° C) | 22.1 |
| Martensite start temperature $M_s$ (° C) | 41.4 |
| Austenite start temperature $A_s$ (° C) | 50.6 |
| Austenite finish temperature $A_f$ (° C) | 68.1 |
| Stress influence coefficient $C_M$ (MPa° $C^{-1}$) | 6.05 |
| Stress influence coefficient $C_A$ (MPa° $C^{-1}$) | 14.25 |
| Young's modulus at 100% austenite $D_A$ (GPa) | 71.7 |
| Young's modulus at 100% martensite $D_M$ (GPa) | 12.5 |
| Critical stress $\sigma_{cr}^P$ (MPa) | 50.6 |
| Critical stress $\sigma_{cr}^{P'}$ (MPa) | 120.3 |
| Maximum recoverable strain $\varepsilon_L$ | 0.045 |
| Wiper-lens friction coefficient $\mu$ | 0.4 |

A first step in designing the modular lens cleaning device 100 is to identify the design materials as well as the related material parameters. A set of commercially available SMA wires (HT Flexinol® Ni-Ti, Dynalloy Inc.) is employed with diameters of 100, 150, 200, 250, 300, and 375 $^{\mu m}$ for measuring the mechanical properties undisclosed by the datasheet, such as transformation temperatures under zero-stress $M_f, M_s, A_s, A_f$, Young's moduli $D_A$ (at the phase of A) and $D_M$ (at the phase of $M_f$), the maximum recoverable strain $\varepsilon_L$, and critical stresses $\sigma_{cr}^P$ and $\sigma_{cr}^{P'}$. The measured parameters are summarized in Table I above.

In one embodiment, a material of the cover lens 16 adopts K9 crystal glass which features 99.4% visible light transmittance. A hydrophobic coating is applied to the external surface of the cover lens that enables the eyelid wiper to remove contaminants with ease.

Embodiments of the eyelid wiper combine two materials: anodized aluminum alloy for holding the SMA wires 102, and ethylene propylene diene monomer (EPDM) rubber with added polytetrafluoroethylene (PTFE). The employed rubber material is able to achieve low contact friction with cover lens ($\mu$=0.4). The eyelid wiper applies about $F_N$=0.3N force against the cover lens. The friction force is estimated as $F_f$=0.12 N.

In consideration of a robotic camera's dimensions, an external diameter of the housing 12 is preferably approximately $\varphi$=16 mm. Three major functions are provided by the housing 12: (1) holding the cover lens in the front of the camera's imaging lens; (2) pairing with the wiper 14 for its rotational motion; and (3) concealing the SMA wires 102 at the structure's edge for actuating the eyelid wiper. The material of the structure is the identical aluminum alloy 6061 used for manufacturing the eyelid wiper. The structural dimensions such as the lever arms $r_1$, $r_2$, and $r_3$ are presented in Table II. Portions formed of aluminum parts are anodized for electrical insulation of the embedded SMA wires.

Figure 13:
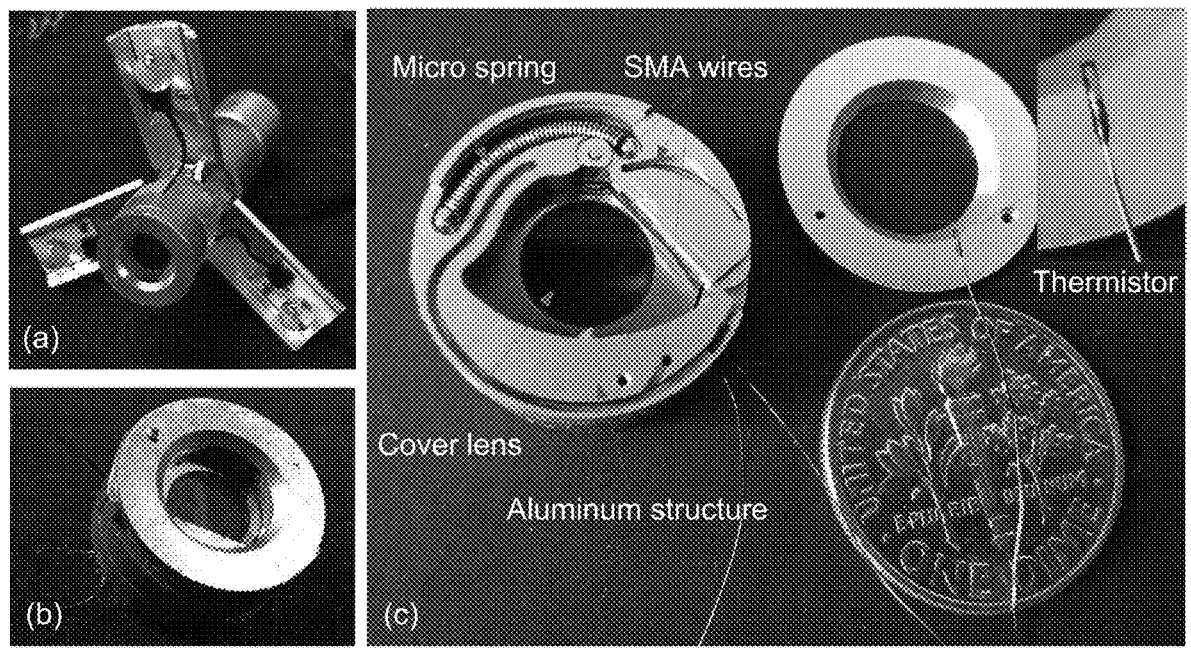
FIG. 13 shows an exemplary embodiment of a lens cleaning device according to one embodiment of the present disclosure.

Phase transformation of SMA wires is associated with temperature change. To control the Joule heating for actuating the wiper 14, a micro thermistor (Fµ3122-07U015, Semitec USA Corp.) is preferably integrated for providing thermal feedback, as illustrated in FIG. 13.

The design of micro extension springs is governed by the force bounds in (1). A set of baseline values are initially assigned to these parameters: $N=2$, $d=0.15$, $r_1/r_2=0.9$, $r_1/r_2=3.2$, $F_N=0.4$. By varying each parameter, the force bounds of $F_s(\Theta)$ are computed by using the data in Table 1, and are illustrated in FIG. 11.

Figure 11:
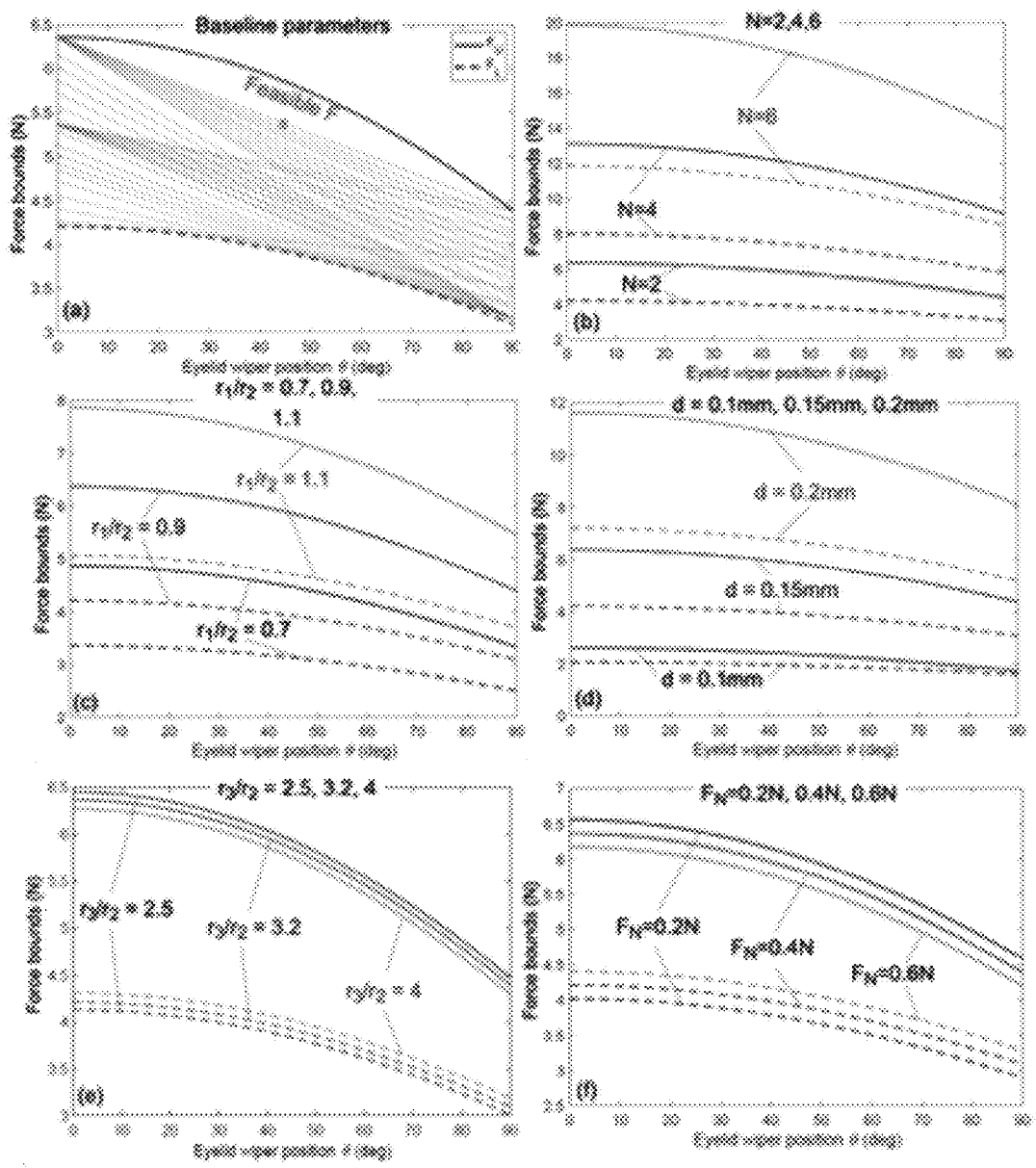
FIG. 11 shows calculated bounds of a spring force of a lens cleaning device according to one embodiment of the present disclosure.

FIG. 11 illustrates the force bounds computed with the baseline parameters. The solid black line represents the upper force bound $F_U$, and the dashed black line represents the lower force bound $F_L$. The values of $F_U$ and $F_L$ are plotted with respect to the wiper's position $\Theta \in [0, \pi/2]$. The red lines exemplify feasible force functions of $F_s(\Theta)$. The maximum and the minimum allowable spring forces is limited at 6.34 and 3.1 when $\Theta=0$ and $\Theta=\pi/2$ respectively. According to (2), $F_s(\Theta=\pi/2)=k\Delta L + F_i$ represents the initial spring force, where $\Delta L \geq 0$.

FIG. 11 shows how the force bounds $F_U$ and $F_L$ change with respect to various values of N, $r_1/r_2$, d, $r_3/r_2$, $F_N$. The parameters N, $r_1/r_2$, d are related to the force of SMA wires in (1) and (3). Therefore, the increasing of these parameters N, $r_1/r_2$, d shifts the force bounds towards higher values. In contrast, the parameters $r_3/r_2$ and $F_N$ impact on the term of the frictional force. The increasing and decreasing of these parameters will lead to the narrowing and expanding of the region between $F_U$ and $F_L$ respectively.

By determining $F_s(\Theta=0)$ and $F_s(\Theta=\pi/2)$, a compatible micro extension spring can be designed with the aid of Advance Spring Design software (Universal Technical Systems, Inc.) according to the desired external diameter, music wire diameter, and body length of the spring.

Figure 12:
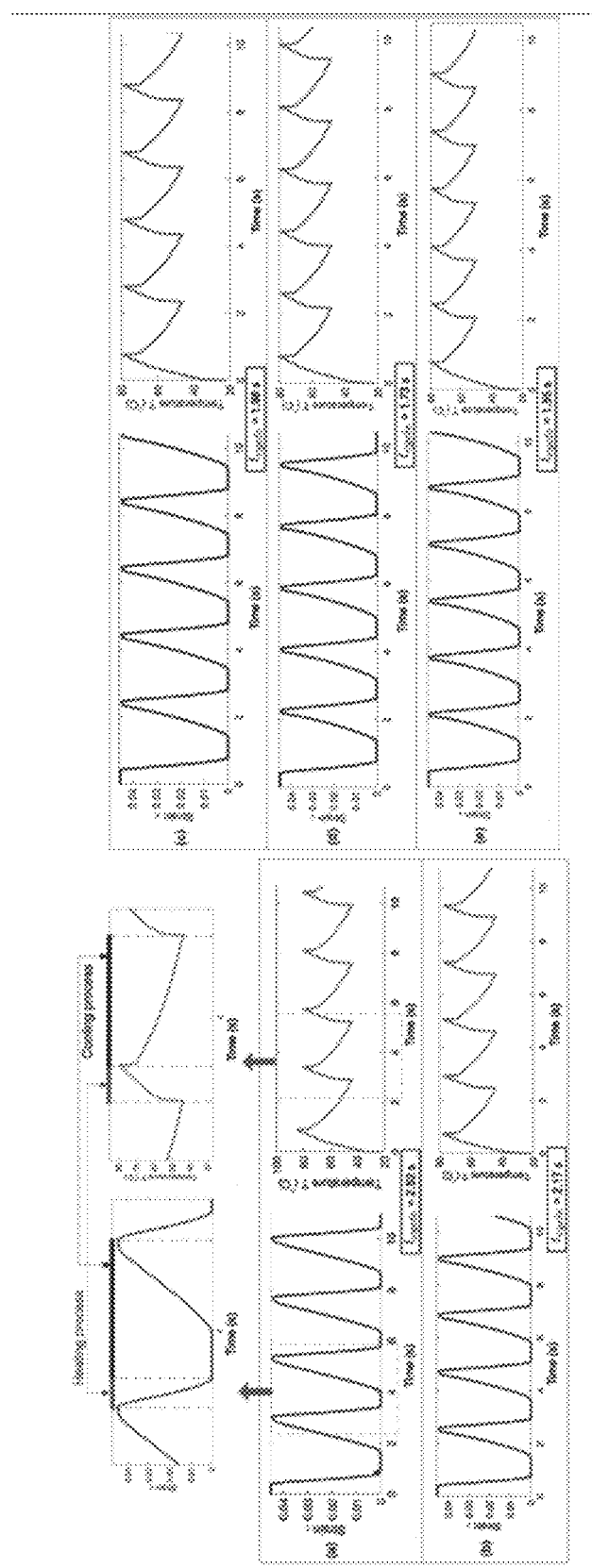
FIG. 12 shows a chart of predicted cycles of strain and temperature of a lens cleaning device according to one embodiment of the present disclosure.

FIG. 12 shows predicted cycles of strain and temperature computed by using different spring parameters. (a) k=0.485 N/mm, $F_i$=2.75 N. (b) k=0.679 N/mm, $F_i$=2.75 N. (c) k=0.873 N/mm, $F_i$=2.75 N. (d) k=0.485 N/mm, $F_i$=3.25 N. (e) k=0.485 N/mm, $F_i$=3.5 N.

Parameters involved in an actuation cycle model are presented in Table II. The polynomial parameters in (14) and (15) are computed as $p_1$=122.63, $p_2$=28.97, $p_3$=0.0098, $q_1$=1165.1, $q_2$=82.67, $q_3$=0.455, $q_4$=1. Based on the identified parameters in Table I and Table II, five sets of feasible extension spring parameters k, $F_i$ (assuming $\Delta L=0$) are investigated: (a)—(0.485 N/mm, 2.75 N), (b)—(0.679 N/mm, 2.75 N), (c)—(0.873 N/mm, 2.75 N), (d)—(0.485 N/mm, 3.25 N), (e)—(0.485 N/mm, 3.5 N). During the heating process, an input current of I=1.5 A was used for Joule heating of SMA wires.

The computed actuation cycles of strain and temperature are demonstrated in FIG. 12. The figures above FIG. 12 show full strain and temperature cycles that include a heating process and a cooling process. In FIG. 12, the first cycle takes longer than the following cycles due to the initial temperature $T=T_\infty$ of the SMA wires. During the cycles, the strain of the SMA wires periodically changes between $\varepsilon=\varepsilon_L$ and $\varepsilon=0$. The actuation cycles $t_{cycle}=t_h+t_c$ vary because of applying different bias loads. The spring parameters are set with an identical initial tension $F_i$=2.75 and increasing spring rates k=0.485, 0.679, 0.873. The actuation cycles are measured as $t_{cycle}$=2.52, 2.17, and 1.98 respectively. While for the spring parameters in FIG. 12 the spring rate is kept identical as k=0.485 N/mm, and the initial tensions are increased as $F_i$=2.75 N, 3.25 N, and 3.5 N. The actuation cycles are measured as $t_{cycle}$=2.52, 1.73, and 1.55.

According to the numerical analysis, the actuation cycle of the eyelid wiper can be reduced by employing a "stronger" spring within the feasible design region. It was observed that the initial tension $F_i$ has greater influence on the actuation cycle than the spring rate k. The prediction accuracy of the actuation cycle is experimentally evaluated as described herein by using the fabricated prototype.

In addition, the parameter $\Delta r$ used in (10) and specified in Table II is estimated because of the irregular shape of aluminum structure surrounding the SMA wires. The values of $\Delta r$ are investigated in the range from 1 to 8 mm which yield insignificant influence on the actuation cycle compared with the spring parameters.

TABLE 2

Actuation Cycle Model Parameters

| 2 Parameters | Value |
| --- | --- |
| $k_a$ Thermal conductivity of 6061 aluminum alloy (W/m - K) | 205 |
| $m_a$ Mass of aluminum structure (g) | 2.5 |
| m Mass of SMA wires (mg) | 4.3 |
| $c_{P_a}$ Specific heat of aluminum (J/kg - K) | 896 |
| $c_p$ Specific heat of SMA (J/kg - K) | 837 |
| $S_a$ Surface area of SMA wires (mm$^2$) | 17.8 |
| $S_b$ Surface area of aluminum structure (mm$^2$) | 351.8 |
| $R_A$ SMA electrical resistivity at austenite ($\Omega$m) | $8 \times 10^{-7}$ |
| $R_M$ SMA electrical resistivity at martensite ($\Omega$m) | $1 \times 10^{-6}$ |
| $\Delta h$ SMA latent of heat transformation (J/kg) | $2.42 \times 10^4$ |
| N Number of SMA wires | 2 |
| h Heat convection coefficient of air (W/m$^2$ - K) | 80 |
| $\Delta r$ Distance between centers of SMA and structure (mm) | 2 |
| $T_\infty$ Ambient temperature (° C) | 23 |
| $\varphi$ Module diameter (mm) | 16 |
| $r_1$ Lever arm length of SMA wires (mm) | 1.2 |
| $r_2$ Lever arm length of spring (mm) | 1.64 |
| $r_3$ Lever arm length of eyelid wiper (mm) | 5.23 |

TABLE 3

Manufactured Micro Extension Spring Parameters

| 2 Parameters | Value |
| --- | --- |
| $\varphi_D$ Outer diameter (mm) | 1.2 |
| $\varphi_I$ Inner diameter (mm) | 0.76 |
| $\varphi_m$ Music wire diameter (mm) | 0.22 |
| k Spring rate (N/mm) | 0.669 |
| $F_i$ Initial tension (N) | 0.62 |
| $L_m$ Body length (mm) | 10.1 |
| $\Delta L$ Spring initial extension (mm) | 3.2 |

FIG. 13 demonstrates an example of a lens cleaning device according to the design parameters in Table I and Table II. FIG. 13 shows the modularized lens cleaning device and the integration of the device in the robotic camera as the camera's sealing cover. FIG. 13 further illustrates the components of the device that include SMA wires, a cover lens, aluminum structures, a micro extension spring, and a thermistor as described herein. Off-the-shelf micro extension springs manufactured by using music wires with the parameters shown in Table III may be suitable for embodiments of the device. The spring rate is very close to the one evaluated in the case of FIG. 12. To match the initial tension to 2.75 as well, the micro spring is elongated with $\Delta L=3.2$ mm when the eyelid wiper's position is at $\Theta=\pi/2$.

The SMA wires are terminated inside the module with the wire leads connecting to a current source. The input current is controlled by using a MOSFET switch and a micro controller. The thermistor connects to the micro controller as well for providing SMA temperature feedback.

Figure 14:
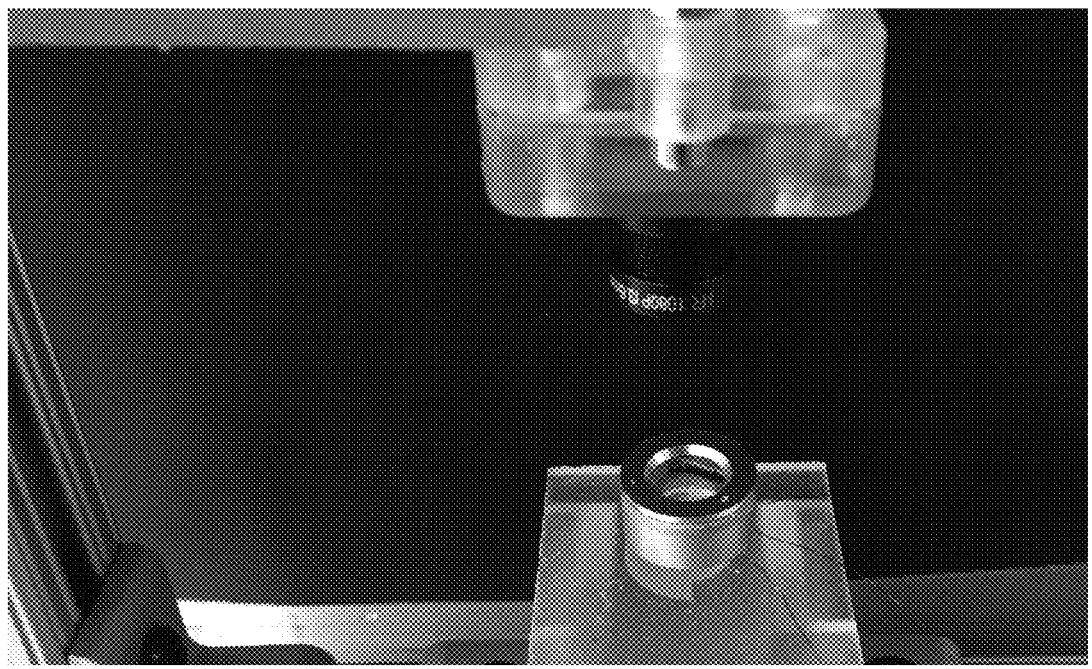
FIG. 14 shows an exemplary embodiment of a platform for recording actuation of a lens cleaning device according to one embodiment of the present disclosure.

To validate an actuation cycle model, an experimental platform may be used for measuring the actuation cycle of the device, as shown in FIG. 14. A camera with 60 FPS (frames per second) is used to record motion of the wiper 14. Modular actuator is held in a fixed position below the recording camera. According to the recorded position $\Theta$ of the eyelid wiper in each frame, the strain cycles of SMA wires can be computed by using (12).

Figure 15A:
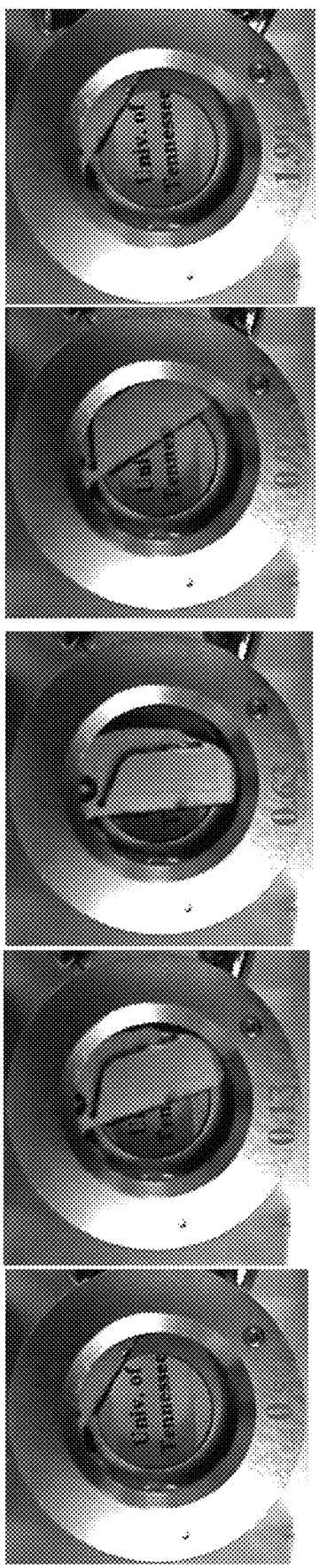
FIG. 15A shows motion of a wiper of a lens cleaning device according to one embodiment of the present disclosure.
Figure 15B:
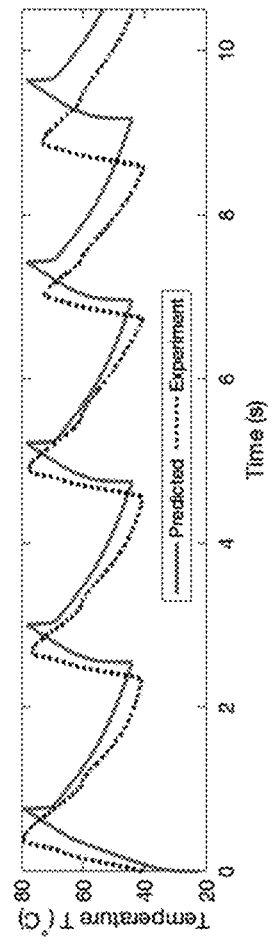
FIG. 15B shows cycling of a wiper of a lens cleaning device according to one embodiment of the present disclosure.

The results of actuation cycle tests are presented in FIG. 15. FIG. 15A shows a set of sampled frames with time stamps to demonstrate the motion of the actuated eyelid wiper. FIG. 15B shows comparison results between the predicted cycles and the measured cycles. Different from the predicted cycles that are consistent in each period, the consistency of measured cycles are influenced by the stability of input current, surrounding air flows, contact between the thermistor and the SMA wires. Therefore, the measured cycle was acquired by averaging 30 cycles as $^-t_{cycle}=2.08$. Comparing with the predicted actuation $t_{cycle}=2.17$, the difference between the predicted and measured cycles is calculated as $^-|t_{cycle}-t_{cycle}^-|/t_{cycle}=4.81\%$.

Three different types of contaminants, i.e. fogging, blood, and bone dusts, were employed to evaluate the cover lens cleaning efficiency of the lens cleaning device 100. Blood and bone dusts were acquired from a piece of fresh cattle meat attached on a bone. To demonstrate the cover lens clarity, a group of letters ("Univ. of Tennessee") are positioned underneath the cover lens, which are shown in FIGS. 14 and 15. In this experiment, the required number of actuation cycles for achieving sufficient clarity of the cover lens were counted.

TABLE 4

Cover Lens Cleaning Test

| 2 2* | Contamination | | |
|---|---|---|---|
| | Fogging | Bone dusts | Blood |
| Cycle number | 1 | 2 | 1 |
| Total time (s) | 1.93 | 4.33 | 2.12 |

Figure 16:
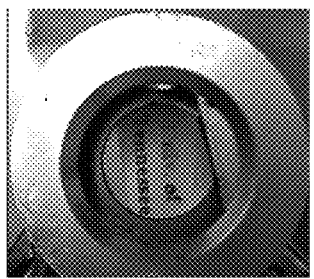
FIG. 16 shows exemplary embodiments of removing debris from a lens with a lens cleaning device according to one embodiment of the present disclosure.
Figure 16:
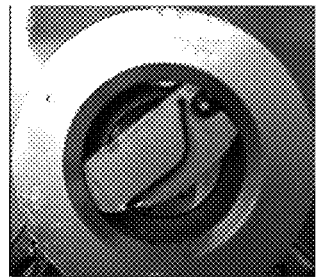
Figure 16:
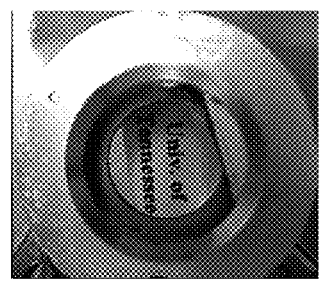
Figure 16:
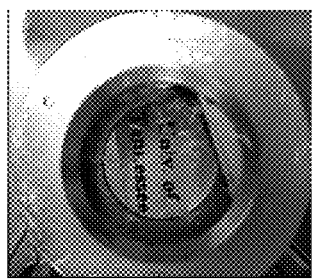
Figure 16:
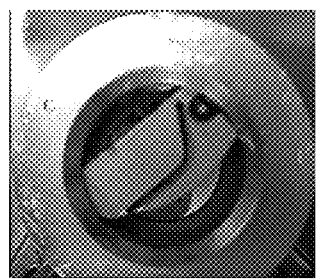
Figure 16:
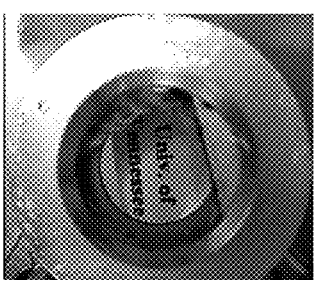
Figure 16:
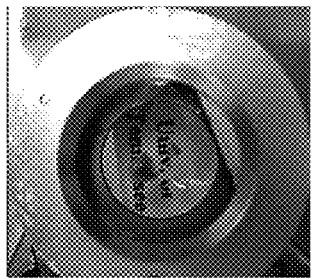
Figure 16:
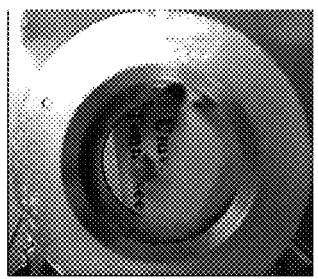
Figure 16:
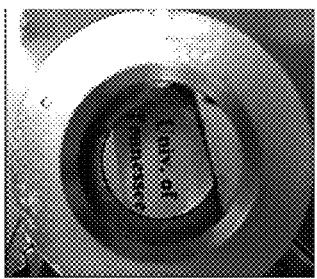

The left figures in FIG. 16 demonstrate that the cover lens is contaminated by fogging, bone dusts, and blood respectively. The middle figures show the sweeping motion by the eyelid wiper for removing the contaminants. The right figures show the cleaning results after one or more actuation cycles. The averaged cycle number and cleaning time used by each case are summarized in Table IV. The experiment results indicate that for fogging and blood conditions, only one cycle are generally needed. The measured cleaning time for these conditions are 1.93 s and 2.12 s respectively. For the case of bone dusts, two consecutive cleaning cycles are generally needed in order to remove all the small particles from the cover lens, which took 4.33 s in total.

Embodiments of the lens cleaning device disclosed herein advantageously allow for uninterrupted and clear visual guidance to surgeons using laparoscopic cameras to manipulate surgical instruments to carry out surgical procedures. Embodiments described herein are readily adaptable to existing cameras to provide clear vision through the cameras during surgical procedures. Further, embodiments of lens cleaning devices disclosed herein are substantially compact and may be used without greatly increasing a size of the laparoscopic camera.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A lens cleaning device comprising:
    a housing shaped to fit over an end of a camera lens of a surgical instrument such that the housing is located around the camera lens of the surgical instrument;
    a wiper movably attached to the housing, the wiper movable across the housing from a first position adjacent a first side of the housing to a second position adjacent a second side of the housing;
    at least one SMA wire mechanically associated with the wiper, the at least one SMA wire located within one of the wiper and the housing located around the camera lens of the surgical instrument;
    wherein when the SMA wire is activated, the wiper is moved between the first position and the second position of the housing such that the wiper sweeps debris from a field of view of the camera lens.

2. The lens cleaning device of claim 1, wherein the wiper is secured to the housing at a hinge.

3. The lens cleaning device of claim 1, further comprising a bias spring coupled at a first end to the housing and at a second end to the wiper, the bias spring biasing the wiper towards one of the first position and the second position on the housing.

4. The lens cleaning device of claim 1, wherein when the wiper is in the first position and the second position, the wiper is substantially within a side edge of the housing such that the wiper does not substantially obstruct a field of view of the camera.

5. The lens cleaning device of claim 4, the housing further comprising one or more gaps formed in sides of the housing such that debris swept by the wiper is evacuated from the housing.

6. The lens cleaning device of claim 1, the housing further comprising a cover lens located on the housing, wherein the wiper contacts the cover lens when the wiper moves between the first position and the second position.

7. The lens cleaning device of claim 6, the cover lens further comprising a hydrophobic layer formed on an upper surface thereof.

8. A lens cleaning device of claim 1, the wiper comprising:

a housing shaped to fit over an end of a camera lens;
a wiper movably attached to the housing, the wiper movable across the housing from a first position adjacent a first side of the housing to a second position adjacent a second side of the housing, the wiper comprising a wiper layer located towards a center of the wiper and along a length of the wiper, the wiper layer extending below the wiper and into contact with a lens surface;
at least one SMA wire mechanically associated with the wiper, the at least one SMA wire associated with the wiper comprising a first set of one or more SMA wires located on a first side of the wiper layer and a second set of one or more SMA wires located on a second side of the wiper;
wherein when the SMA wire is activated, the wiper is moved between the first position and the second position of the housing such that the wiper sweeps debris from a field of view of the camera lens; and
wherein activation of the first set of one or more SMA wires urges the wiper towards the first position and wherein activation of the second set of one or more SMA wires urges the wiper towards the second position.

9. The lens cleaning device of claim 8, further comprising a first reinforcement layer on the first side of the wiper layer and a second reinforcement layer on the second side of the wiper layer.

10. The lens cleaning device of claim 8, further comprising:
a slide track located around a portion of the housing;
a slide bar located on an end of the wiper and slidably engaged with the slide track;
wherein the slide bar slides along a length of the slide track when the wiper moves between the first position and the second position.

11. The lens cleaning device of claim 10, further comprising:
a first magnet proximate a first end of the slide track; and
a second magnet proximate a second end of the slide track;
wherein the slide bar is formed of a ferrous material; and
wherein the first magnet releasably anchors the wiper in the first position; and
wherein the second magnet releasably anchors the wiper in the second position.

12. A lens cleaning device comprising:
a housing shaped to fit over an end of a camera lens;
a wiper movably attached to the housing, the wiper movable across the housing from a first position adjacent a first side of the housing to a second position adjacent a second side of the housing, the wiper including
a wiper layer located towards a center of the wiper and along a length of the wiper, the wiper layer extending below the wiper,
a first SMA wire layer located on a first side of the wiper layer along a length of the wiper, and
a second SMA wire layer located on a second side of the wiper layer along a length of the wiper;
wherein when the first SMA wire layer is activated, the wiper is moved between the first position and the second position on the housing.

13. The lens cleaning device of claim 12, the wiper further comprising a first reinforcement layer located between the first SMA wire layer and the wiper layer and a second reinforcement layer located between the second SMA wire layer and the wiper layer.

14. The lens cleaning device of claim 12, further comprising:
a slide track located around a portion of the housing;
a slide bar located on an end of the wiper and slidably engaged with the slide track;
wherein the slide bar slides along a length of the slide track when the wiper moves between the first position and the second position.

15. The lens cleaning device of claim 14, further comprising:
a first magnet proximate a first end of the slide track; and
a second magnet proximate a second end of the slide track;
wherein the slide bar is formed of a ferrous material; and
wherein the first magnet releasably anchors the wiper in the first position; and
wherein the second magnet releasably anchors the wiper in the second position.

16. The lens cleaning device of claim 12, wherein when the wiper is in the first position and the second position, the wiper is substantially within a side edge of the housing such that the wiper does not substantially obstruct a field of view of the camera.

17. The lens cleaning device of claim 16, the housing further comprising one or more gaps formed in sides of the housing such that debris swept by the wiper is evacuated from the housing.

18. The lens cleaning device of claim 12, the housing further comprising a cover lens located on the housing, wherein the wiper contacts the cover lens when the wiper moves between the first position and the second position.

19. The lens cleaning device of claim 18, the cover lens further comprising a hydrophobic layer formed on an upper surface thereof.

20. A lens cleaning device comprising:
a housing shaped to fit over an end of a camera lens;
a slide track located around a portion of the housing;
a wiper pivotally attached to the housing at a first end of the wiper, the wiper movable across the housing from a first position adjacent a first side of the housing to a second position adjacent a second side of the housing, the wiper comprising a wiper portion that is in contact with a lens surface;
a slide bar located on a second end of the wiper and slidably engaged with the slide track;
at least one SMA portion located on the wiper;
wherein when the SMA wire is activated, the wiper is moved between the first position and the second position of the housing such that the wiper sweeps debris from a field of view of the camera lens;
wherein the slide bar slides along a length of the slide track when the wiper moves between the first position and the second position.

* * * * *